(12) United States Patent
Adams et al.

(10) Patent No.: US 7,518,723 B2
(45) Date of Patent: *Apr. 14, 2009

(54) SYSTEMS AND METHODS FOR DETECTING RADIATION, BIOTOXIN, CHEMICAL, AND BIOLOGICAL WARFARE AGENTS USING A MULTIPLE ANGLE LIGHT SCATTERING (MALS) INSTRUMENT

(75) Inventors: John A. Adams, Escondido, CA (US); Kristina M. Crousore, Oceanside, CA (US); Cherish K. Teters, San Diego, CA (US); John Ricardi, Camarillo, CA (US); David L. McCarty, Cincinnati, OH (US); Michael Tutrow, Solana Beach, CA (US)

(73) Assignee: JMAR Technologies, Inc., San Diego, CA (US)

( * ) Notice: Subject to any disclaimer, the term of this patent is extended or adjusted under 35 U.S.C. 154(b) by 35 days.

This patent is subject to a terminal disclaimer.

(21) Appl. No.: 11/564,777

(22) Filed: Nov. 29, 2006

(65) Prior Publication Data

US 2007/0195324 A1 Aug. 23, 2007

Related U.S. Application Data

(63) Continuation-in-part of application No. 11/539,166, filed on Oct. 5, 2006, which is a continuation-in-part of application No. 11/381,346, filed on May 2, 2006, which is a continuation-in-part of application No. 11/231,350, filed on Sep. 19, 2005.

(51) Int. Cl.
*G01N 21/00* (2006.01)
*G01N 15/02* (2006.01)

(52) U.S. Cl. .................... 356/338; 356/336
(58) Field of Classification Search .............. None
See application file for complete search history.

(56) References Cited

U.S. PATENT DOCUMENTS

| 4,548,473 A | 10/1985 | Lo et al. |
| 4,548,500 A | 10/1985 | Wyatt et al. |
| 4,710,025 A | 12/1987 | Wyatt et al. |
| 4,716,123 A | 12/1987 | Wood |
| 4,752,226 A | 6/1988 | Akers et al. |
| 4,906,440 A | 3/1990 | Kolesar, Jr. |
| 5,721,433 A | 2/1998 | Kosaka |
| 5,866,430 A | 2/1999 | Grow |
| 5,922,183 A | 7/1999 | Rauh |
| 5,962,853 A | 10/1999 | Huth-Fehre et al. |
| 5,965,882 A | 10/1999 | Megerle et al. |
| 6,016,712 A | 1/2000 | Warden et al. |
| 6,347,374 B1 | 2/2002 | Drake et al. |
| 6,421,121 B1 | 7/2002 | Haavig et al. |

(Continued)

Primary Examiner—Michael P Stafira
(74) Attorney, Agent, or Firm—Baker & McKenzie LLP

(57) ABSTRACT

A particle detection system to identify and classify particles is programmed to capture digitized images of the particle generated by directing a light source through a fluid that includes the particle. The particle scatters the light and the scattered light is detected using a detector. The detector creates a digital signal corresponding to the particle, which is used by the system to generate a Bio-Optical Signature. This Bio-Optical Signature can then be used to classify the event, or particle. A count rate of the classified particles is monitored to detect a change that is representative of a toxin attack.

64 Claims, 22 Drawing Sheets

U.S. PATENT DOCUMENTS

| | | |
|---|---|---|
| 6,515,737 B2 | 2/2003 | Perry |
| 6,519,033 B1 | 2/2003 | Quist et al. |
| 6,541,627 B1 | 4/2003 | Ono et al. |
| 6,569,384 B2 | 5/2003 | Greenbaum et al. |
| 6,573,992 B1 | 6/2003 | Drake |
| 6,590,652 B2 | 7/2003 | Quist et al. |
| 6,628,386 B2 | 9/2003 | Davis et al. |
| 6,630,990 B2 | 10/2003 | van't Oever et al. |
| 6,639,672 B2 | 10/2003 | Haavig et al. |
| 6,760,107 B1 | 7/2004 | Drake |
| 6,774,995 B2 | 8/2004 | Quist et al. |
| 6,859,277 B2 | 2/2005 | Wagner et al. |
| 6,934,022 B1 | 8/2005 | Engelhardt |
| 6,964,857 B2 | 11/2005 | Greenbaum et al. |
| 6,972,424 B1 | 12/2005 | Quist et al. |
| 7,057,724 B1 | 6/2006 | Mead et al. |
| 7,072,038 B2 | 7/2006 | Quist et al. |
| 2002/0186372 A1 | 12/2002 | Haavig et al. |
| 2003/0035105 A1 | 2/2003 | Quist et al. |
| 2003/0086087 A1 | 5/2003 | Quist et al. |
| 2003/0090657 A1 | 5/2003 | Drake |
| 2003/0107734 A1 | 6/2003 | Davis et al. |
| 2004/0201845 A1 | 10/2004 | Quist et al. |
| 2005/0151968 A1 | 7/2005 | Drake et al. |
| 2006/0261941 A1 | 11/2006 | Drake et al. |
| 2007/0013910 A1* | 1/2007 | Jiang et al. .................. 356/336 |

* cited by examiner

FIG. 28
2 MICRON SPHERE
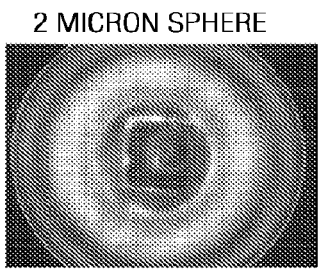
4 MICRON SPHERE
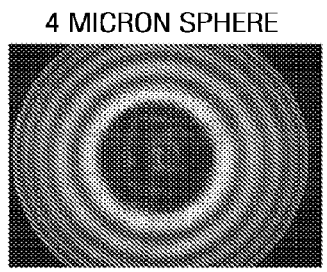
8 MICRON SPHERE
CRYPTO
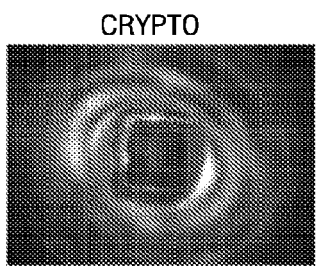
INORGANIC "DIRT"
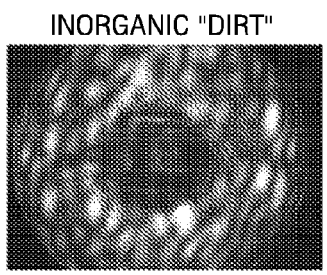
GIARDIA
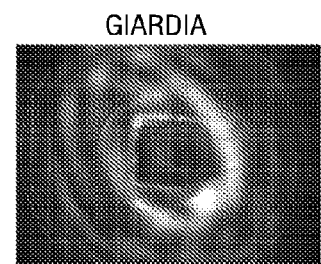
E. COLI
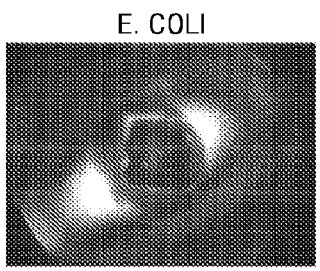

SYSTEMS AND METHODS FOR DETECTING RADIATION, BIOTOXIN, CHEMICAL, AND BIOLOGICAL WARFARE AGENTS USING A MULTIPLE ANGLE LIGHT SCATTERING (MALS) INSTRUMENT

FIELD OF THE INVENTION

This application claims the priority as a Continuation-In-Part (CIP) under 35 U.S.C. 120 to U.S. patent application Ser. No. 11/539,166, entitled "Systems and Methods For Detection and Classification of Waterborne Particles Using a Multiple Angle Light Scattering (MALS) Instrument," filed Oct. 5, 2006, which is in turn a CIP of U.S. patent application Ser. No. 11/381,346 entitled "Systems and Methods For a High Capture Angle, Multiple Angle Light Scattering (MALS) Instrument," filed May 2, 2006, which is in turn a CIP of U.S. patent application Ser. No. 11/231,350, entitled "Systems and Methods For Detecting Scattered Light From a Particle Using Illumination Incident at an Angle," filed Sep. 19, 2005, all of which are incorporated herein by reference as if set forth in full.

BACKGROUND

1. Field of the Invention

Embodiments described herein relate to detecting and classifying particles in a liquid using multi-angle-light-scattering (MALS), and in particular to detecting and classifying biological agents, such as bacteria and bacterial spores, and to detecting other agents that can cause the destruction of natural bacterial particles normally present in water, such as chemical, biotoxin, or radiation agents.

2. Background of the Invention

A major concern for municipal and commercial water treatment facilities is the detection and control of pathogenic microorganisms, both known and emerging, in potable water treatment and distribution. There are not only a number of chlorine resistant pathogens such as *Cryptosporidium* that can contaminate drinking water systems, but also potentially harmful microorganisms that can be introduced, either accidentally or intentionally, and propagate under suitable environmental conditions. Due to the length of time for standard laboratory methods to yield results, typically 24-72 hours, there has not been a reliable system to detect microbial contaminants in real-time and on-line to provide a warning of pathogen contamination events. Because of these expanding challenges, there has been an accelerated development of rapid tests and real-time methods to address the pressing needs of the water treatment community.

Conventional microbiological methods can be used to detect some harmful microorganisms; however, such methods provide limited results. Analytical methods in microbiology were developed over 120 years ago and are very similar today. These methods incorporate the following steps: sampling, culturing and isolating the microbes in a suitable growth media by incubation, identifying the organisms through microscopic examination or stains, and quantifying the organisms. *Cryptosporidium* and *Giardia* form oocysts or cysts and cannot easily be cultured in conventional ways. To detect these protozoan pathogens, an amount of water containing suspected pathogens, typically 10 liters, is sent through a special filter to collect and concentrate the organisms. Then the filter is eluted and the organisms further processed by staining the organisms and sending the concentrated solution through flow cytometry for example. These procedures, which can be found in Standard Methods (EPA 16.23) or ASME, require ascetic technique in sampling and handling, skilled technicians to perform the analysis, and a number of reagents, materials, and instruments to obtain results. Practically, such methods have proved to be time consuming, costly, and of little effectiveness for many current environmental field applications.

In order to reduce the amount of time to access microbiological results, a number of methods have been developed, mostly in the field of medicine. These faster tests have been improved and adapted to the environmental field and are generally categorized as 1) accelerated and automated tests 2) rapid tests and 3) contamination warning systems (CWS).

Accelerated tests are by grab sample and results can be obtained in 4 hours to 18 hours. Accelerated tests include immunoassays, ATP luminescence, and fluorescent antibody fixation. Rapid tests are also by grab sample and require manipulation of the sample to 'tag' the microbes with an identifiable marker or concentrate the microbe's genetic material (DNA) for subsequent identification. Results are normally available in 1-3 hours. These types of tests include Polymerase Chain Reaction (PCR) and Flow Cytometry.

Real time contamination warning systems are continuous warning devices that detect contaminants and provide an 'event' warning within minutes to prompt further investigation or action. CWS include laser based multi-angle light scattering (MALS) and multi-parameter chemical & particle instruments that detect water quality changes inferring potential biological contamination. Continuous, real time detection of pathogens in water surveillance was first tried in the late 1960's and has progressed through a series of development steps until the first public field demonstration in 2002.

When light strikes a particle a characteristic scattering pattern is emitted. The scattering pattern encompasses many features of the particle including the size, shape, internal structures (morphology), particle surface, and material composition. Each type of microorganism will scatter light giving off a unique pattern herein called a Bio-Optical Signal (BOS). Photo-detectors collect the scattered light and capture the patterns which are then sent to a computer for analysis.

In addition to detecting biological pathogens in the water that occur naturally or are introduced intentionally by terrorists, it can be desirable to also monitor for the presence of toxins such as; microbial toxins for example, botulism; chemical toxins for example, Aldicarb, Nicotine, Cyclohex-imide, Sodium Arsenate, or Sodium Fluoroacetate; or radiation generating alpha, beta, or gamma radiation; any of which chemical, biological, or radiation (CBR) agents that may also be present.

Various sensors have been used to monitor water quality for chemical agent attack. Currently available water quality sensor technology is based generally on adaptations, modifications, and extensions of conventional analytical chemistry equipment and techniques. Some examples follow.

U.S. Pat. No. 5,965,882 issued on Oct. 12, 1999 to Megerle et al. describes a miniaturized ion mobility spectrometer sensor cell that comprised an improved spectrometer for detecting chemical warfare agents and hazardous vapors.

U.S. Pat. No. 5,922,183 issued on Jul. 13, 1999 to Rauh describes a metal oxide matrix. Thin film composites of the oxides and biological molecules such as enzymes, antibodies, antigens and DNA strands can be used for both amperometric and potentiometric sensing.

U.S. Pat. No. 5,866,430 issued on Feb. 2, 1999 to Grow describes a methodology and devices for detecting or monitoring or identifying chemical or microbial analytes. The described methodology comprises four basic steps: (1) The gas or liquid medium to be monitored or analyzed is brought into contact with a bioconcentrator which is used to bind with or collect and concentrate one or more analytes. (2) The bioconcentrator-analyte complex is then exposed to radiation of one or more predetermined wavelengths to produce Raman scattering spectral bands. (3) At least a portion of the Raman spectral bands is collected and processed by a Raman spectrometer to convert the same into an electrical signal. And (4) the electrical signal is processed to detect and identify, qualitatively and/or quantitatively, the analyte(s).

U.S. Pat. No. 4,906,440 issued on Mar. 6, 1990 to Kolesar describes a sensor for detecting chemicals. In this sensor a gas detector is described that detects the presences of the gas when the gas reacts with a distributed RC notch network to cause a shift in operating frequency and notch depth. A metallic/metallic oxide gas sensitive discontinuous film acts as the distributive resistive element in the RC notch network. The gas changes the conductivity of the film and this causes the network to react. In the preferred embodiment, a copper/cuprous oxide film detects organophosphorus compounds, which can be chemical warfare agents.

U.S. Pat. No. 4,752,226 issued on Jun. 21, 1988 to Akers et al. describes a method for simulating chemical warfare attack that includes the use of a radiant energy transmitting device for radiating energy in a pattern which simulates different types and forms of chemical agents. Protective devices, such as gas masks, protective clothing, or structures, are provided with sensors for determining whether the protective device is properly employed.

U.S. Pat. Nos. 6,569,384 and 6,964,857 issued on May 27, 2003 and Nov. 15, 2005 respectively to Greenbaum et al. describe using changes in the natural fluorescence from naturally occurring organisms in the water to monitor for chemical attack.

All of these sensors and methods leave something to be desired in terms of accuracy, efficiency, cost or some combination thereof.

There are also many systems that measure gamma radiation directly in water, fewer that measure beta radiation, and still fewer that measure alpha radiation. Generally the alpha radiation detectors dry our a water sample and then measure the alpha radiation in air or vacuum.

Presently, a detection system capable of meeting all of the 'ideal detection system' parameters, e.g., as cited by the American Water Works Association does not exist. Conventional devices and methods often differ in the amount of time to obtain results, degree of specificity, sampling frequency, concentration sensitivity, operating complexity, and cost of ownership.

SUMMARY

A particle classification system uses a two dimensional array of pixel sensors to measure scattered light generated by a particle in a liquid medium, when a laser beam is incident on the particle. These scattering measurements are then automatically analyzed through the use of a computer and algorithms to generate a classification of the particle causing the scattering. When the particles transit the laser beam, light is scattered in all directions and is described by MIE scattering theory for particles about the size of the wavelength of light or larger. Rayleigh scattering is used when the particles are much smaller than the wavelength of light. By monitoring the quantity of the detected organisms the detection system is able to determine whether undesired organisms are present in the water or whether undesired toxins, chemical, biological, or radiation, may be present in the water.

These and other features, aspects, and embodiments of the invention are described below in the section entitled "Detailed Description."

BRIEF DESCRIPTION OF THE DRAWINGS

Features, aspects, and embodiments of the inventions are described in conjunction with the attached drawings, in which:

FIG. 28 shows representative images from a 2, 4, and 8 micron diameter polystyrene spheres, from *Cryptosporidium*, dirt, *Giardia*, and *E.coli* obtained using a particle detection system in accordance with one embodiment;

DETAILED DESCRIPTION OF THE PREFERRED EMBODIMENTS

Figure 1:
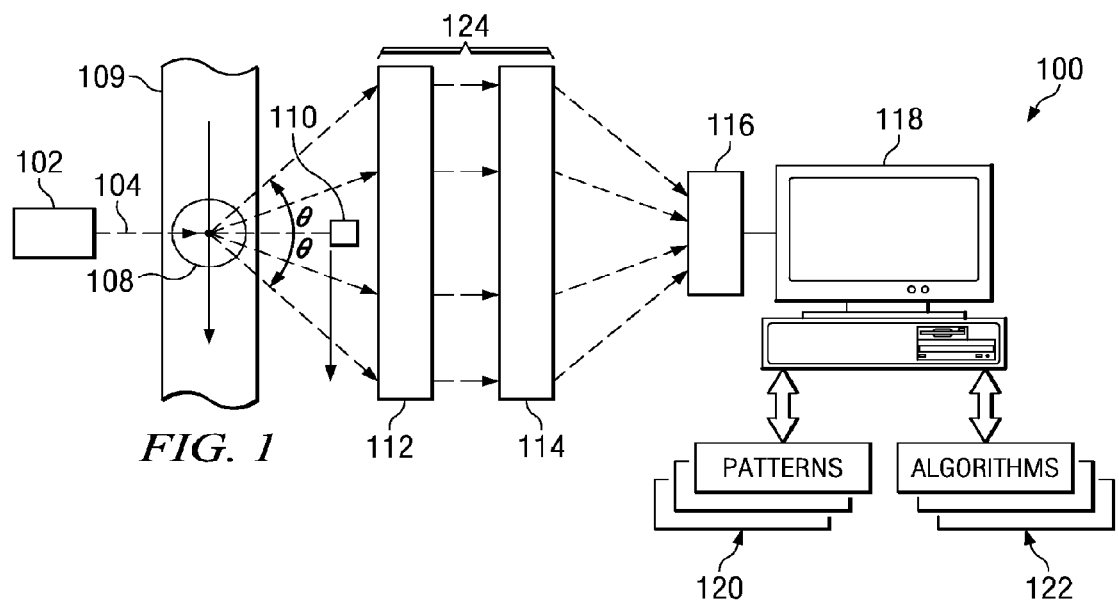
FIG. 1 is a diagram illustrating an example embodiment of a particle detection system.

In the following description, all numbers disclosed herein are approximate values, regardless whether the word "about" or "approximately" is used in connection therewith. They may vary by up to 1%, 2%, 5%, or sometimes 10 to 20%. Whenever a numerical range with a lower limit, $R_L$, and an upper limit $R_U$, is disclosed, any number R falling within the range is specifically and expressly disclosed. In particular, the following numbers R within the range are specifically disclosed: $R=R_L+k*(R_U-R_L)$, wherein k is a variable ranging from 1% to 100% with a 1% increment, i.e. k is 1%, 2%, 3%, 4%, 5%, ..., 50%, 51%, 52%, ..., 95%, 96%, 97%, 98%, 99%, or 100%. Moreover, any numerical range defined by two numbers, R, as defined in the above is also specifically disclosed. It is also emphasized that in accordance with standard practice, various features may not be drawn to scale. In fact, the dimensions of the various features may be arbitrarily increased or reduced for clarity of discussion.

Certain embodiments described herein provide a method for real-time particle detection that uses advancements in computing power, special optics, photonics engineering, advanced signal processing, and complex algorithms, in order to provide a MALS detection system that provides simplicity, cost effectiveness, speed, and reliability. The systems described in the embodiments below are analytical systems using MALS where a side stream from a water source flows through a transparent flow cell. A laser directs a beam of light into the flow cell and through the water stream. In certain embodiments, the water is first characterized for background interferences to distinguish foreign particles from the pathogens' signatures resulting in a custom detection library in each particular installation.

In operation, particles pass through the beam, the scattered light is emitted and captured by the detectors, converted to a digital signal, and finally sent to the computer's microbial library for analysis. When a pattern is recognized by the library, the organisms are classified within minutes. The data can be transmitted to a user screen and remote communications equipment. In certain embodiments, upon reaching a pre-set threshold level, an 'alert' can be generated and an instantaneous sample can be automatically extracted for further identification and confirmation.

Water, or other liquids for that matter, can be monitored continuously as it passes through the flow cell at a defined rate. This provides a much higher probability of detecting and classifying microorganisms compared to intermittent grab samples. The speed and performance can be further enhanced when the 1) microbial concentration level is high, 2) the water, or liquid, is of high 'clarity' or purity, 3) microorganisms match defined Bio-Optical Signatures in the library versus an 'unknown', and 4) the particles are of larger size, e.g., >1 micron, giving distinct scattering patterns.

In certain embodiments, if an unclassified organism is detected, the system can categorize it as an 'unknown' and still provide an 'alert' if a certain threshold level is reached.

Thus, the systems and methods described below can provide valuable early warnings of potential microbial contamination. The system described can be implemented economically and with extremely low operating costs. Further, the systems described do not use reagents or require costly consumables and can be compact, rugged, and easy to use, while requiring minimal operator training or expertise. In certain embodiments, 'warning' and 'alert' levels can be adjusted according to the requirements of a particular implementation and can interface with a number of communication protocols to provide immediate information for quality control or security personnel.

FIG. 1 is a diagram illustrating an example particle detection system configured in accordance with one embodiment of the systems and methods described herein. Many of the embodiments described below are used for detecting microorganism such as *Cryptosporidium* and *Giardia*; however, it will be understood that the systems and methods described herein can be used to detect any particle capable of detection using the systems and methods described, such as bacteria and yeasts. Bacteria are typically smaller than *Cryptosporidium* and *Giardia* ranging from 500 nanometers diameter upwards to 2 microns and from oval to rod shape. Yeasts are typically the size of *Giardia* or larger. Further, while the embodiments described below generally describe detected particles in water, it will be understood that the systems and methods described can be used to detect particles in other liquids, and even in other media such as air.

System 100 comprises a light source 102 configured to provide illumination 104 to a target area 108. In the embodiment of FIG. 1, target area 108 is within a fluid cell 106. Water intended to be interrogated for various particles, or microorganisms can flow through flow cell 106, e.g., in a downward direction as indicated. Illumination 104 will encounter particles in target zone 108, which will cause the illumination to scatter in a manner different than the illumination transmitted through the surrounding fluid medium.

System 100 can also comprise an optical system 124. Optical system 124 can comprise several elements. For example, optical system 124 can comprise a lens, or lens system 112 as well as an optical element 114. The system 100 can also comprise a detector, detector system, or detector array 116, which can be interfaced with a processing system 118.

Light source 102 can be configured to deliver a structured light pattern, or illumination. Thus, light source 102 can be, e.g., a coherent light source, such as a laser. Depending on the embodiment, light source 102 can comprise a single light source, such as a single laser, or a plurality of light sources, such as a plurality of lasers. Further, the wavelength of the light source can be at a fixed wavelength. Alternatively, when multiple light sources are used, the light sources can have several discrete wavelengths.

Accordingly, light source 102 can be a laser configured to produce a laser beam 104. When laser beam 104 strikes a particle within target area 108, the particle will cause the beam to scatter in a pattern that is different than the pattern produced due to beam 104 traveling through the water flowing in flow cell 106. Optical system 124 can be configured to then pick up the scattered light and direct it onto detector 116.

Detector 116 can actually be a plurality of detectors, such as a plurality of detectors arrayed in different positions around target area 108. Alternatively, detector 116 can comprise an array of photo detectors. For example, in one embodiment, detector 116 can actually comprise a linear array of photo detectors configured to detect the scattered light and generate an electrical signal having an amplitude corresponding to the amplitude of the detected light. In one implementation for example, a Charge Coupled Device (CCD) can be used for detector 116. CCDs are readily available with thousands of pixels, wherein each pixel can form an individual photo detector. In another implementation for example, a 2 dimensional array of photodiodes or avalanche photodiodes of 64, 128, 256, or 512 total pixels can be used to increase the total dynamic range of the detector as compared to a CCD.

Detector 116 can be configured to generate an electrical signal, or signals, reflective of the light pattern incident on detector 116. The signals can then be provided to processing system 118 for further analysis. As described above, processing system 118 can convert the signals into a pattern using various algorithms 122. Processing system 118 can also comprise the memory configured to store a plurality of Bio-Optical Signatures, or patterns 120 that are associated with various particles, or microorganisms of interest.

Thus, processing system can compare the pattern generated using algorithms 122 to one of the stored patterns 120 in order to identify particles within target zone 108.

As mentioned above, algorithms 122 and patterns 120 can be used to determine many features of particles being identified within target zone 108, e.g., including the size, shape, internal structures or morphology, particle surface, and material composition, i.e., organic or inorganic. For example, certain embodiments can use Multiple Analysis Of Variance (MANOVA) algorithms, neural networks, simulated annealing, algorithm independent machine learning, physiologic, grammatical methods, and other algorithmic techniques for pattern generation and recognition. It will be understood, however, that the systems and methods described herein are not limited to any specific algorithms for techniques, and that any algorithm or technique, or a combination thereof, that could be used to perform the processes described herein can be used as required by a particular implementation.

Particles within target zone 108 will cause light from laser beam 104 to scatter as illustrated in FIG. 1. Light scattering from target zone 108 at an angle greater than Θ from the optical axis of beam 104 will be internally reflected within flow cell 106 at the interface of flow cell 106 with the external atmosphere. Thus, only light at angles less than Θ can escape and be picked up by optical system 124.

In certain embodiments, a spherical lens (not shown) completely surrounding the flow cell, except for the flow cell inlet and outlet, can be placed at the interface of flow cell 106 in order to allow light scattered at any angle to the lens to pass through the lens to optical system 124. Of course, including such a spherical lens increases the complexity and cost of system 100.

Light passing through target zone 108 along the optical axis of beam 104 will generally be of a much greater intensity than that of the scattered light beams. The intensity of the beam along the optical axis can be so great that it can essentially prevent, or degrade detection of the scattered light beams. Accordingly, a beam stop 110 can be included in order to deflect beam 104 and prevent it from entering optical system 124 and being detected by detector 116.

The light scattered by a particle within target zone 108 can enter optical system 124, which can comprise an optical element 114. Optical element 114 can be configured to direct the scattered light onto detector 116. Specifically, optical element 114 can be configured in such a way that it can direct light traveling along a given path to an appropriate position on detector 116 or to an appropriate detector within an array of detectors comprising detector 116. For example, in one embodiment, optical element 114 can be a holographic optical element constructed so that each refracting section refracts, or redirects light from one of the scattered paths so that it falls on the correct location of detector 116. In other embodiments, optical element 114 can comprise a zone plate lens that can be configured to map the distance from the central optical access to a unique mapping that is useful for high speed scanning.

In certain embodiments, the scattered light may need to be collimated after it passes through target zone 108. Thus, a converging lens 112 can be included in optical system 124. A converging lens can be configured to reduce the angle spread for the various scattered light rays. In other words, a converging lens can be configured to collimate or converge the spread light rays. In other embodiments, some other optical device can be used to collimate the scattered light rays. It will also be apparent, that certain embodiments may not need an optical lens 112, i.e., collimation may not be necessary depending on the embodiment. Thus, optical system 124 may or may not contain an optical lens 112, or a collimator, as required by the specific implementation.

As mentioned above, detector 116 can actually comprise a plurality of detectors such as a linear detector array or 2 dimensional array such as a Charge Coupled Device (CCD) or for better dynamic range, a 2 dimensional array of photodiodes or avalanche photodiodes. In one embodiment, for example, detector 116 can actually comprise a linear photo diode camera, e.g., a 128-pixel linear photo diode camera. In another embodiment, a square array of photodiodes may be used for detector 116. In yet another embodiment, an array of photodiodes arranged in segmented concentric circles may be employed for detector 116.

Generally, optical element 114 will be selected so as to complement detector 116 by directing the scattered light rays onto the appropriate pixel, or a section of detector 116; however, in certain embodiments, optical element 114 may not be needed. For example, in certain embodiments, the scattered light rays are incident directly onto detector 116.

Figure 2:
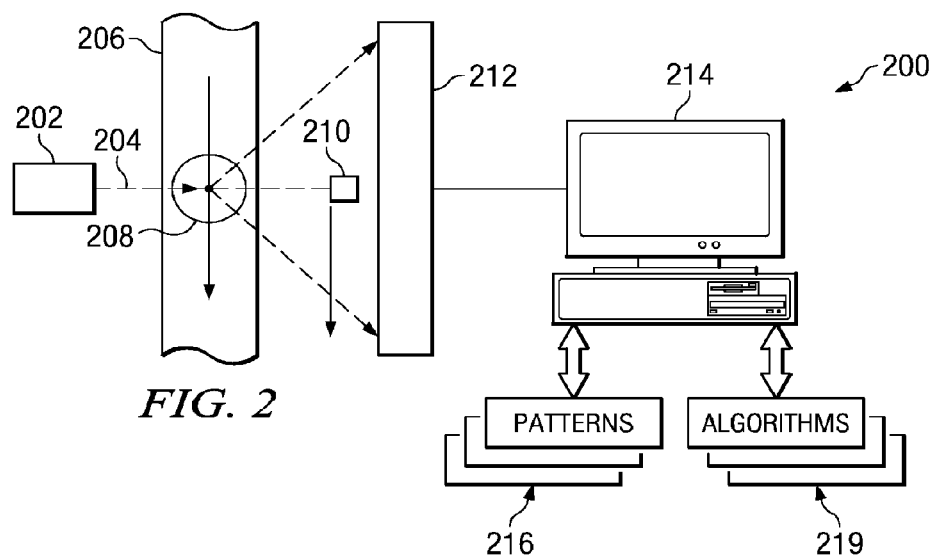
FIG. 2 is a diagram illustrating another example embodiment of a particle detection system.

FIG. 2 is a diagram of a particle detection system 200 that does not include an optical element. Thus, system 200 comprises a light source 202, such as a laser, that produces a beam 204 that is incident on particles in target zone 208 within a fluid flowing in flow cell 206. The particles scatter beam 204 and the scattered beams are then incident directly on a detector 212. Detector 212 then produces electrical signals based on the incident scattered light rays and provides the electrical signals to processing system 214. Processor system 214 can, like processing system 118, be configured to generate a pattern from the electrical signals using algorithms 219 and compare them against stored patterns 216 in order to identify particles within target zone 208.

In the embodiment of FIG. 2, a beam stop 210 is still required to reflect the light ray traveling along the optical axis.

For example, in one embodiment, detector 212 can comprise a 64-pixel detector array, while in other embodiments, detector 212 can comprise a 128-pixel detector array. In certain embodiments, it can be preferred that detector 212 comprise a 256-pixel detector. Arrays larger than 256-pixels can be utilized in the present invention at a penalty of increasing cost and complexity. It should also be noted, that detector 212 can comprise conditioning amplifiers, multiplex switches, an Analog-to-Digital Converter (ADC) configured to convert analog signals produced by the detector pixel elements into digital signals that can be passed to processing system 214. An example embodiment of a detector is described in more detail below with respect FIG. 14.

Further, system 200 can include multiple lens optics, with spatial filters, to delivered the scattered light from the particle in the target zone with less optical noise.

As mentioned above, each type of particle, or microorganism, will scatter light giving off a unique pattern called an Bio-Optical Signature. A detector, such as detector 212, can collect the scattered light and capture the patterns. Electrical signals representative of the pattern can then be provided to a processing system such as processing system 214. FIGS. 3 and 4 illustrate example Bio-Optical Signatures for two different types of particles.

Figure 3A:
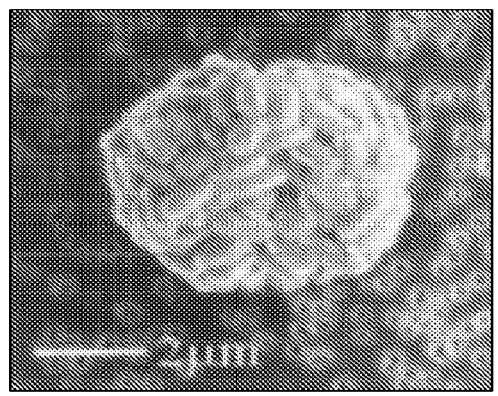
FIG. 3A is a picture of *B. subtilis* spores.
Figure 3B:
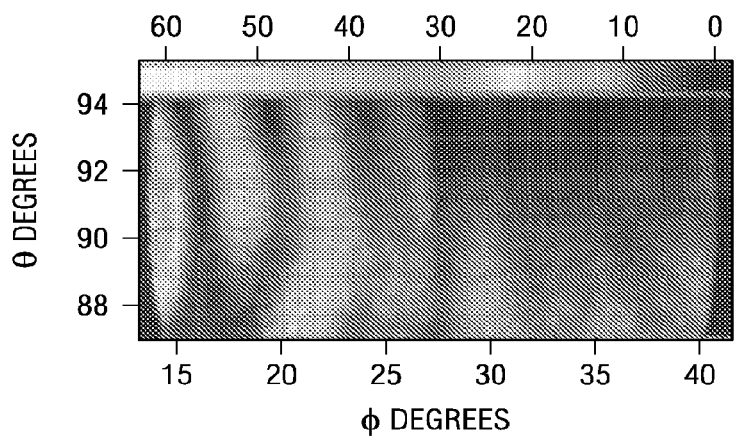
FIGS. 3B and 3C are pictures illustrating example Bio-Optical Signatures that can be generated by the systems of FIGS. 1 and 2 for the *B. subtilis* spores of FIG. 3A.
Figure 3C:
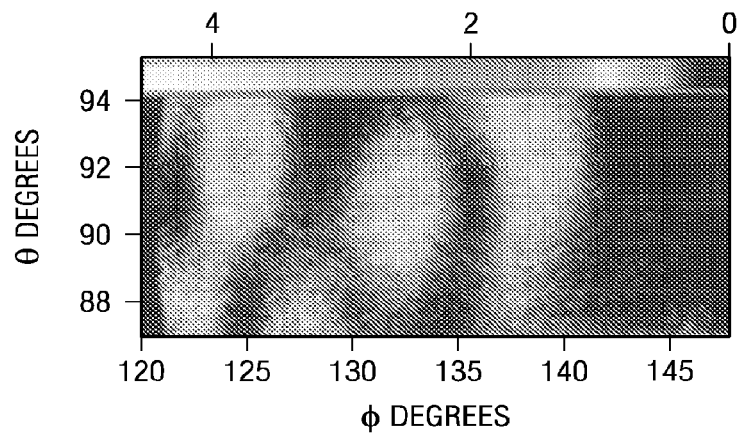
Figure 4A:
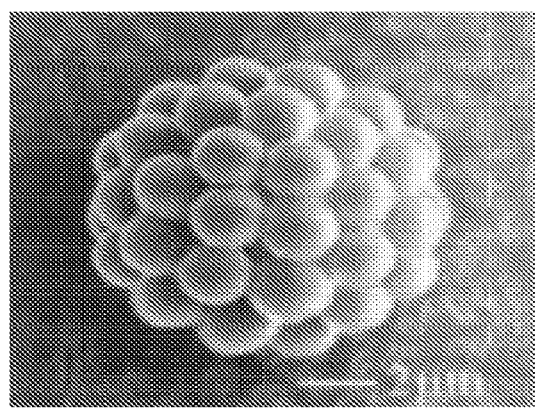
FIG. 4A is a picture of a ball of polystyrene latex spheres.
Figure 4B:
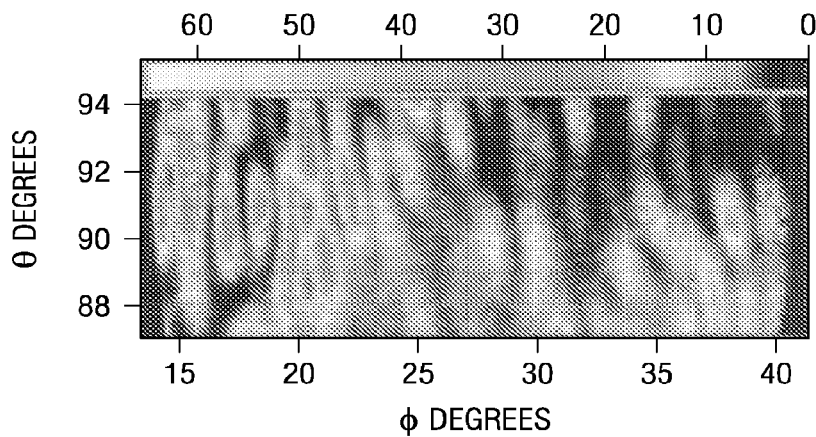
FIGS. 4B and 4C are pictures illustrating example Bio-Optical Signatures that can be generated by the systems of FIGS. 1 and 2 for the ball of plastic spheres of FIG. 4A.
Figure 4C:
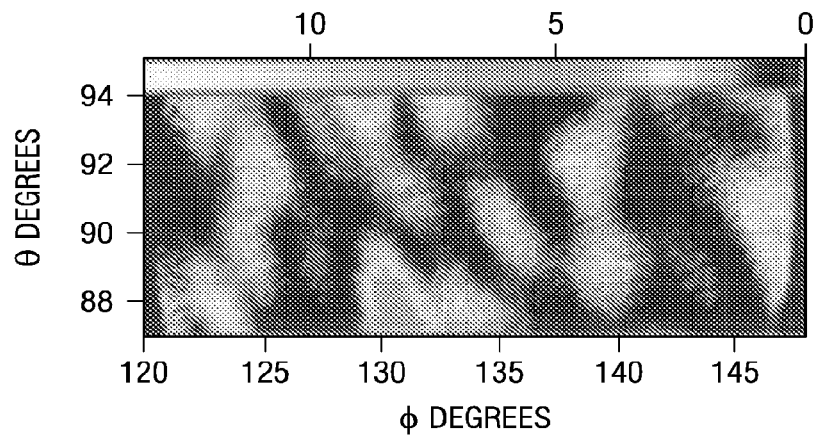

FIG. 3A is a picture illustrating *B.subtilis* spores, a microorganism. FIGS. 3B and 3C are pictures illustrating the Bio-Optical Signatures associated with the *B.subtilis* spores of FIG. 3A. FIG. 4A is a picture illustrating a ball of plastic spheres. FIGS. 4B and 4C are diagrams illustrating the Bio-Optical Signature for the ball of plastic spheres in FIG. 4A. Thus, the Bio-Optical Signatures, or patterns, of FIGS. 3A-3B and 4A-4B, which can be produced using, e.g., algorithms 218, can be compared to patterns stored within the processing system.

Figure 5:
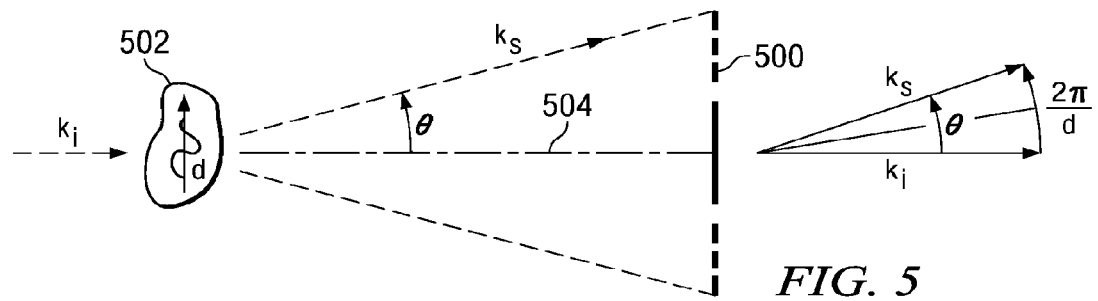
FIGS. 5-7 are diagrams illustrating a technique for using illumination incident at an angle in a light scattering detection system, such as the systems of FIGS. 1 and 2.

As noted above, if some form of spherical lens, or other device, is not used, then only scattered light rays with an angle less the $\Theta$ would be detected; however, if the illumination beam is incident at an angle, then light can be measured through twice the original measured scattering angles and still be captured by the detector. The ratio of the scattered light intensity from larger scattering angles to the smaller scattering angles approaches unity as the particle size decreases. Thus smaller particles scatter light into proportionately larger angles. Illuminating the sample at angle permits radiation scattered at large angles from smaller particles to still be captured by the by the detector's optical system thus, a greater resolution can be achieved. This is illustrated by FIGS. 5-7.

When illumination is incident upon a particle 502 along an optical axis 504, vector $k_i$ can be used to represent the illumination. As illumination incident along vector $k_i$ encounters particle 502, it will be scattered through a sphere of 360 degrees but only detected through a range of angles up to $\Theta$. Thus, a scattered light ray at the outer edge of the detector range can be represented by vector $k_s$.

Figure 6:
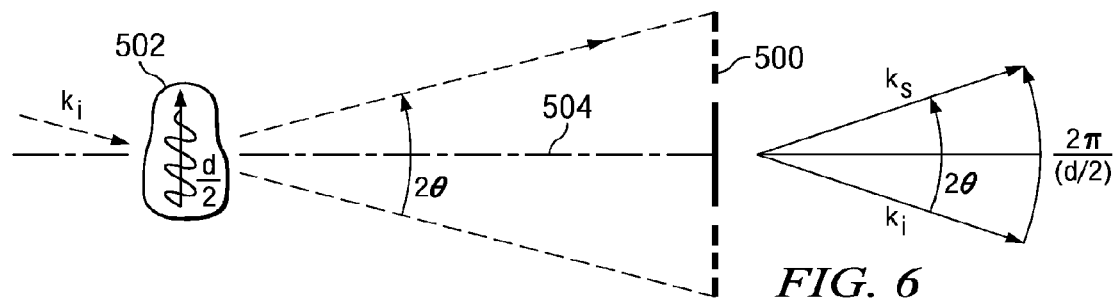

If, however, the illumination is incident at an angle illustrated by vector $k_i$ in FIG. 6, then the detector will be able to see light scattered through a greater angles. For example, the scattered light rays will be measured through an angle of $2\Theta$. As a result, objective 500 can collect scattered light rays scattered through twice the angle as compared to the system in FIG. 5. Thus, the resolution of the system illustrated in FIG. 6 would be twice that of the system illustrated in FIG. 5.

Figure 7:
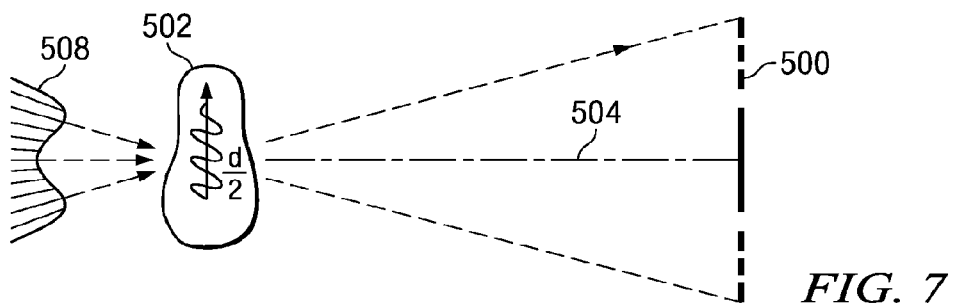

FIG. 7 is a diagram illustrating that the same effect can be achieved using a plurality of incident beams 508 that include beams incident at an angle from above and below the optical axis 504. Switching on or off the individual laser beams can provide additional multiple angles without having to provide additional detectors. If the switching is fast enough compared to the transit of the particle through the beam, then the additional angles can be obtained for the same particle.

It should be noted that objective 500 in FIGS. 5-7 can be a zone plate as well as another conventional optical element, including a holographic optical element.

Figure 9:
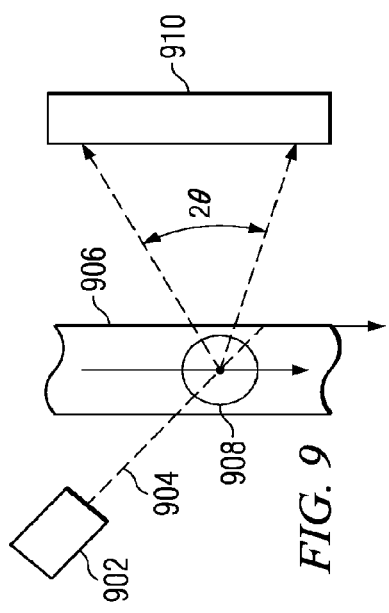
FIG. 9 is a diagram illustrating an example particle detection system that implements the technique of FIGS. 5-7 in accordance with another embodiment.
Figure 8:
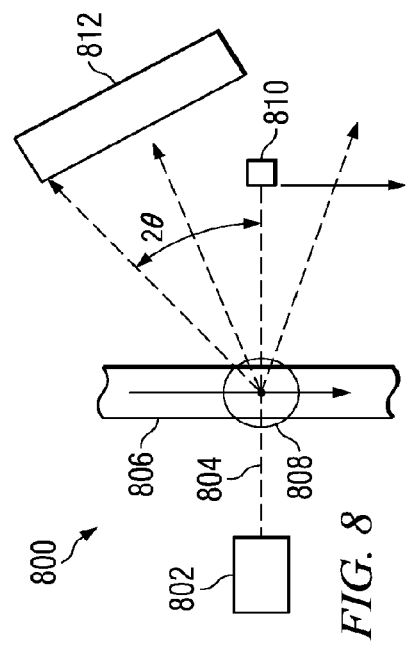
FIG. 8 is a diagram illustrating an example particle detection system that implements the technique of FIGS. 5-7 in accordance with one embodiment.

FIGS. 8 and 9 illustrate that the technique depicted in FIGS. 6 and 7 could be achieved by altering the position of the optical detector or by configuring the light source so that the illumination is incident at an angle upon the target zone. Thus, FIG. 8 is a diagram illustrating an example particle detection system 800 in which an optical detector 812 has been repositioned so as to capture scattered light rays scattered to an angle $2\Theta$. In FIG. 8, a light source 802, such as a laser, produces a beam 804 that is incident on particles within target zone 808. It should be noted that a beam stop 810 can still be required within system 800 to deflect the beam traveling along the optical axis.

It will be understood that system 800 can comprise a processing system, but that such system is not illustrated for simplicity.

FIG. 9 is a diagram illustrating an example particle detection system 900 in which optical source 902 is configured such that beam 904 is incident upon target zone 908 at an angle equal to or greater than the critical angle defined by the phenomenon of total internal reflection. In the system of FIG. 900, by selecting the incident angle such that the beam experiences total internal reflection, beam 904 is internally reflected within flow cell 906, and thus a beam stop is not required. This can lower the cost and complexity of system 900 and can, therefore, be preferable.

Again, it will be understood that system 900 can comprise a processing system, but that such system is not illustrated for simplicity.

As mentioned above with respect to FIG. 1, angles larger than $\theta$ will be reflected internally within flow cell 106. In general, collecting high angle scattered light from an object in a liquid medium requires some mechanism to prevent the internal reflection of the high angles being sought. This problem can be referred to as Total Internal Reflection (TIR) of the high angle scattered light. TIR can occur at high to low indexes of refraction interfaces within the optics of the instrument, or system being used to observe or collect the scattered light, e.g., the interface between flow cell 106 and the external atmosphere.

In certain embodiments, a second surface curved mirror reflecting optic can be used to collect and reflect the light. Such an optic can allow easy capture of light angles up to 90° for all azimuthal angles, when the sample is index coupled with the non-reflecting surface of the collection optic. Such an optic can prevent TIR issues at angles greater than approximately 40°.

Figure 10:
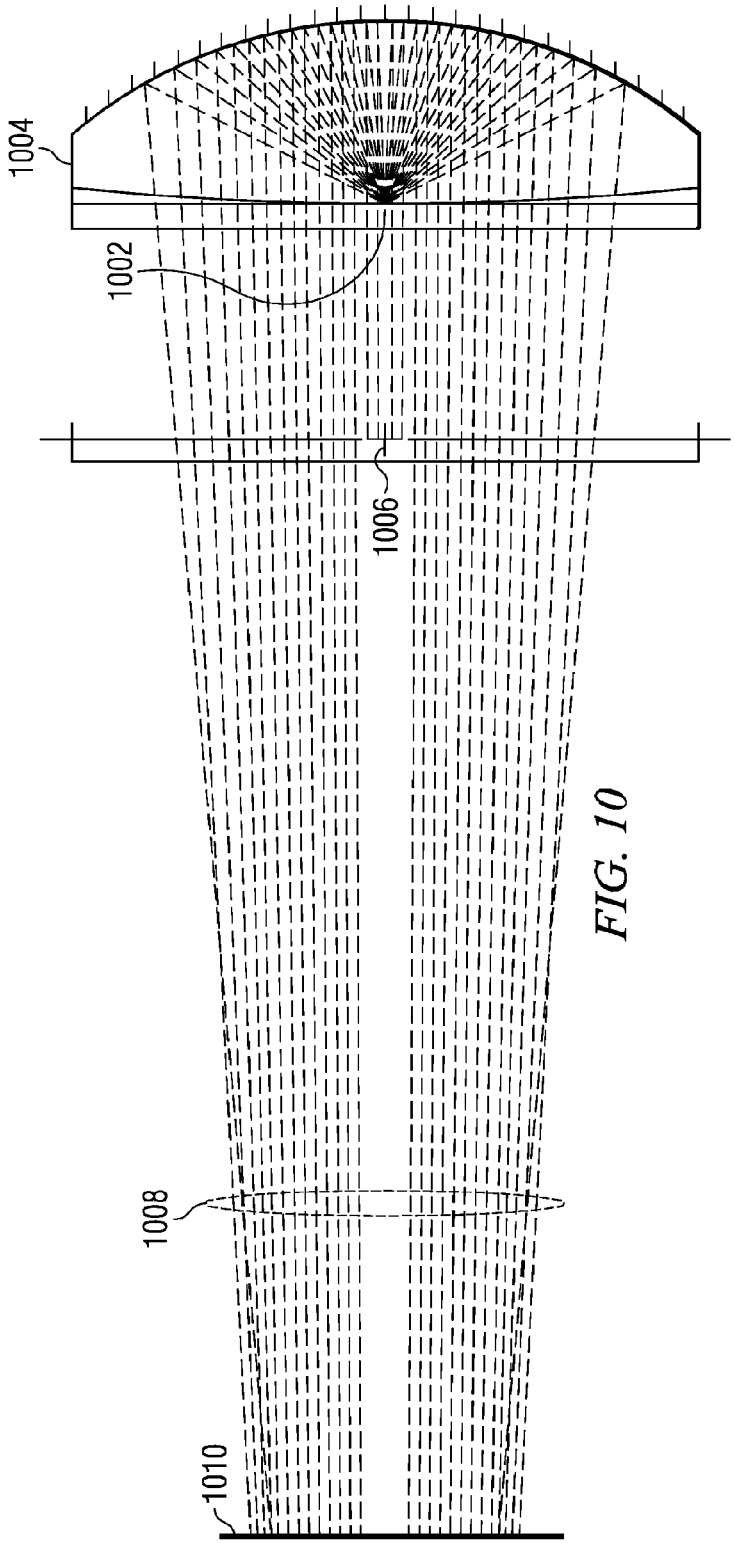
FIG. 10 is a diagram illustrating a spectrometer ray trace for light scattered by a particle suspended in a liquid medium and reflected by a curved mirror as shown in FIG. 13.

FIG. 10 is a diagram illustrating a scatterometer ray trace for light scattered by a particle 1002 and collected using a second surface curved mirror 1004. In the example of FIG. 10, light reflected through an angle of 60° by the reflective surface of mirror 1004 corresponds to light scattered through an angle of 900 by object 1002. The scattered light 1008 passes by beam stop 1006, which is configured to reflect the high intensity light traveling along the beam axis. Scattered light can then be incident on a detector surface 1010, such as a CCD.

Figure 11:
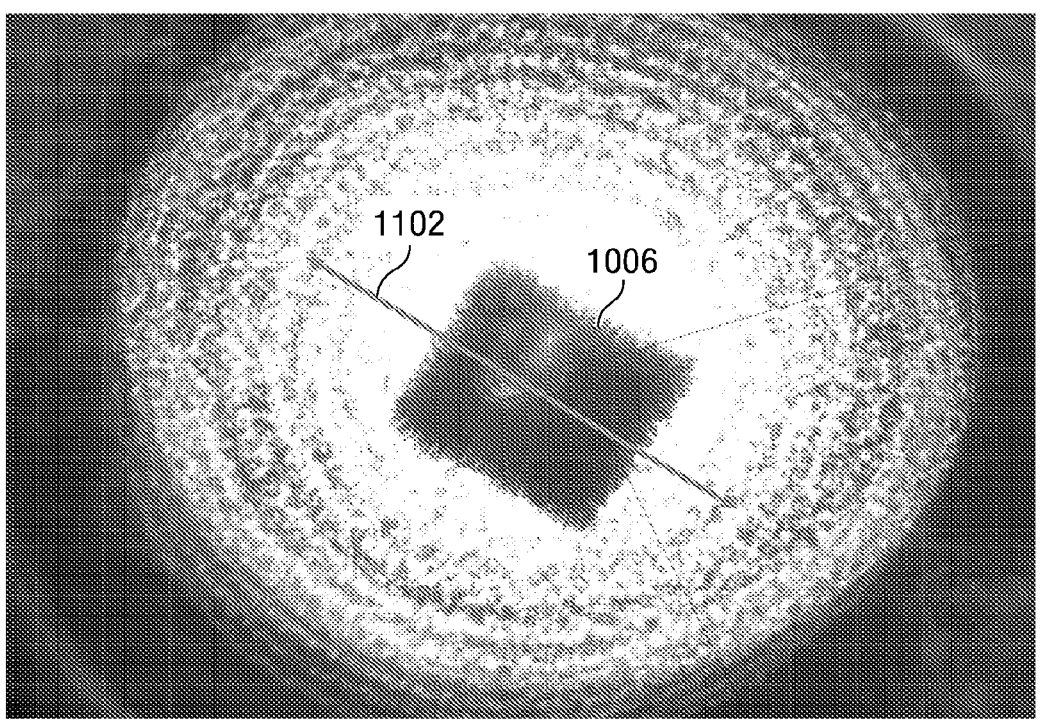
FIG. 11 is a image illustrating the scattered light pattern produced by the particle of FIG. 10.

FIG. 11 is a diagram illustrating a pattern produced by scattered light 1008 incident on detector 1010. The pattern depicted in FIG. 11 corresponds to the diffraction pattern generated by a sphere comprising a diameter of approximately 8 microns. Line 1102 is drawn along the laser polarization axis. Beam stop 1006 reflects light along the beam axis.

Figure 12:
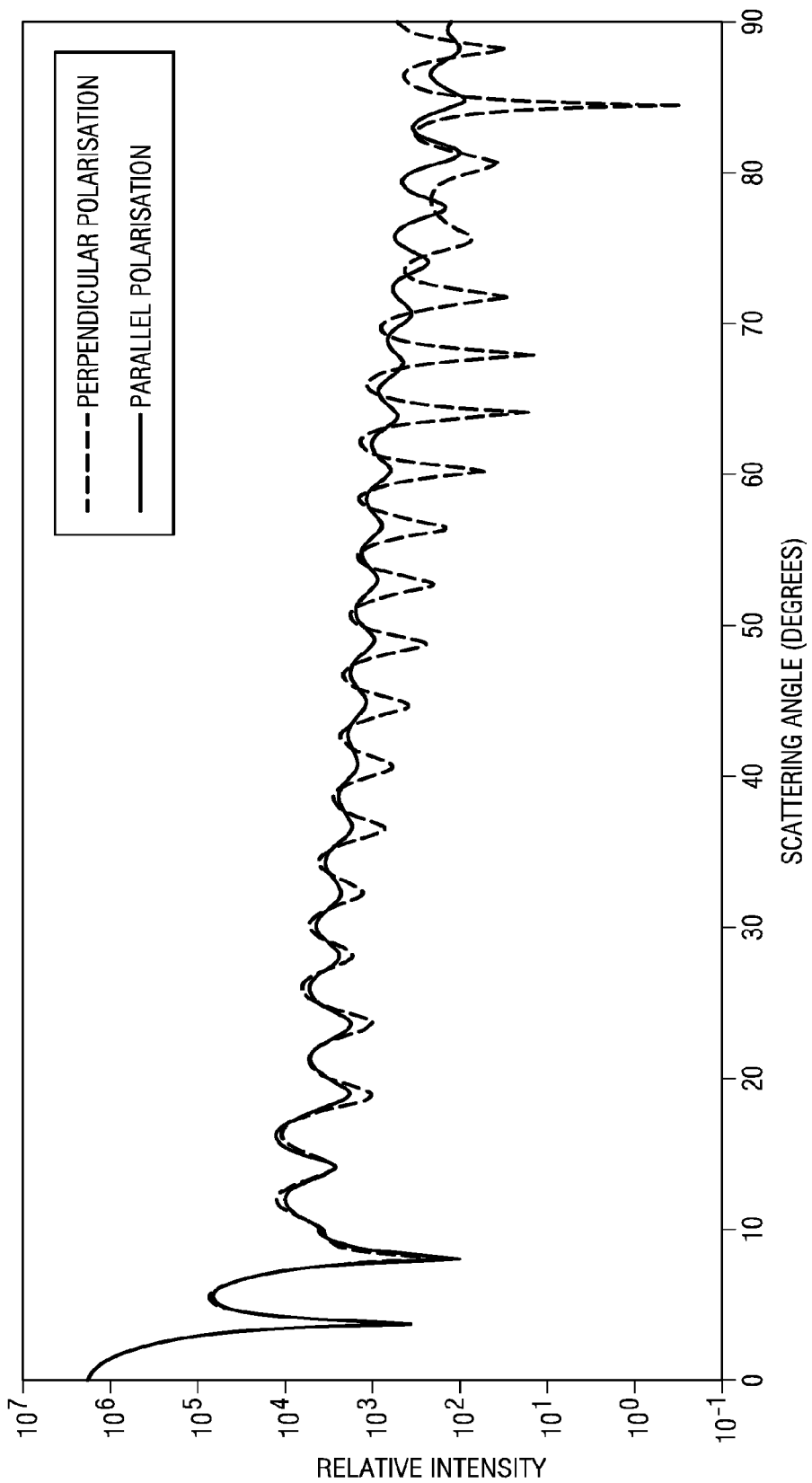
FIG. 12 is a graph illustrating the relative intensity of the scattered light versus the scattering angle.

FIG. 12 is a graph illustrating the relative intensity of scattered light versus the scatter angle for the pattern of FIG. 11. As can be seen, light scattered through large angles can be detected using optic 1004.

Thus, for example, a reflective optic, such as optic 1004 can be included in systems such as systems 100 and 200. An optic such as optic 1004 can be included in place of, or in addition to other optics within the system. This can increase the angle θ through which scattered light can be collected and detected. Although, systems 100 and 200 are just examples of the types of systems that can make use of a second surface curved mirror for collecting and detecting high angle scattered light as describe above. Accordingly the embodiments described with respect to FIGS. 10-12 should not be seen as limited to implementation in systems such as systems 100 and 200.

Figure 13:
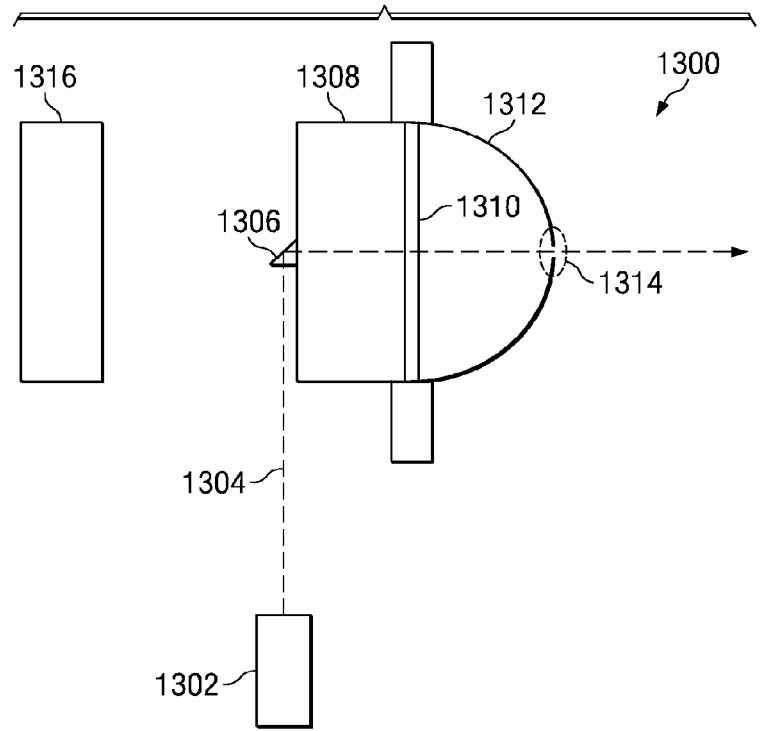
FIG. 13 is a diagram illustrating a system configured to collect light scattered by a particle and reflected by a curved reflective optic.

For example, FIG. 13 is a diagram illustrating a particle detection system 1300 configured to collect light scattered by a particle and reflected by a curved reflective optic as described above. System 1300 comprises a laser 1302 configured to generate a laser beam 1304. Beam 1304 can be directed at a 45 degree reflective silver prism 1306, which can cause beam 1304 to go through interface optic 1308, flow cell 1310, and reflective optic 1312 through unsilvered area 1314 on reflective optic 1312. Thus, silver prism 1306 and unsilvered area 1314 on reflective optic 1312 allow beam 1304 to be removed from the desired signal, much as beamstop 1006 does in alternative embodiments.

Interface optical element 1308 can be a separate element optically coupled to flowcell 1310 with a coupling medium, or integral to the design of flow cell 1310. Reflective optical element 1312 can also be a separate element optically coupled to flowcell 1310 with a coupling medium or integral to flowcell 1310. The scattered radiation pattern produced by an object in flowcell 1310 is reflected by reflective optical element 1312. The reflected light then falls on 2-dimensional photo detector array 1316.

Figure 14:
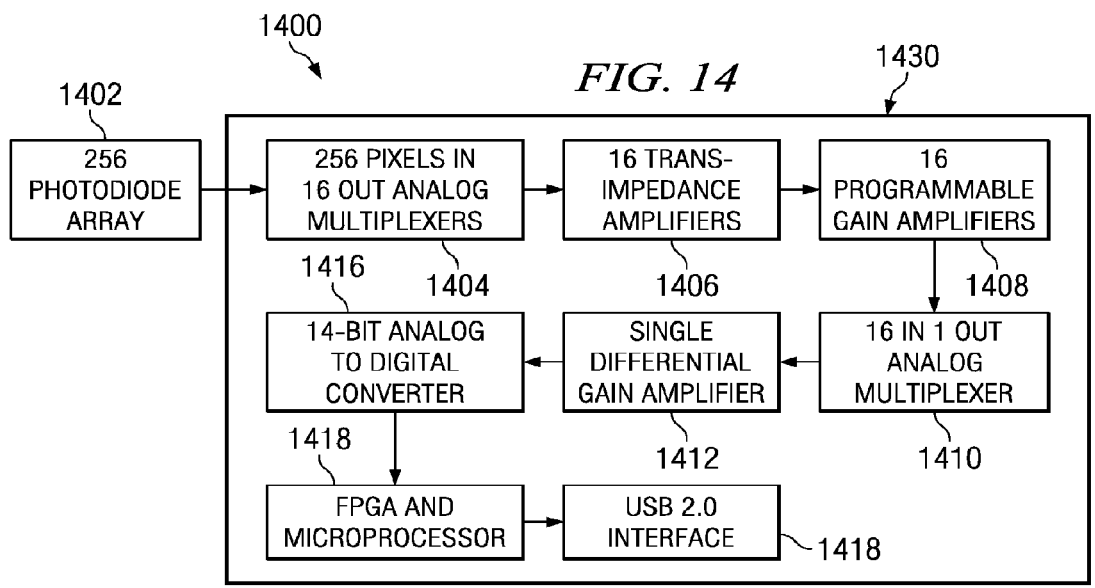
FIG. 14 is a diagram illustrating an example detector system interfacing a 2-dimensional detector array to processing electronics.

FIG. 14 is a diagram illustrating an example detector system 1400, such as detector 212 or a system including array 1316. In the example of FIG. 14, system 1400 comprises a 256-pixel detector packaged array 1402 removably attached to a signal conditioning and digitizing board 1430. Board 1430 can comprise signal conditioning amplifiers 1406 and 1408, multiplex analog switches 1404 and 1410, a 14-bit Analog to Digital Converter (ADC) 1416, a microcontroller 1418, and a USB2.0 communications chip 1420. Thus, system 1400 can be packaged as a complete high-speed USB 2.0 camera operating at frame rates of 1,000 frames per second upwards to 12,000 frames per second.

Detector system 1400 can be configured to process and digitize data captured by detector 1402 and to pass this data, e.g., via USB chip 1420, to a computing system for analysis. For example, as explained above the data can be passed to a processing system 118, which can be configured to use algorithms for system 118, which can be configured to use algorithms 122 to process and analyze the data. FIGS. 15-20 are flow charts illustrating example processing steps that can be carried out by a processing system such as system 118. A combination of compiled C++ and compiled Matlab 2006a software code can be used to continue a comprising system to perform to methods described herein.

Figure 15:
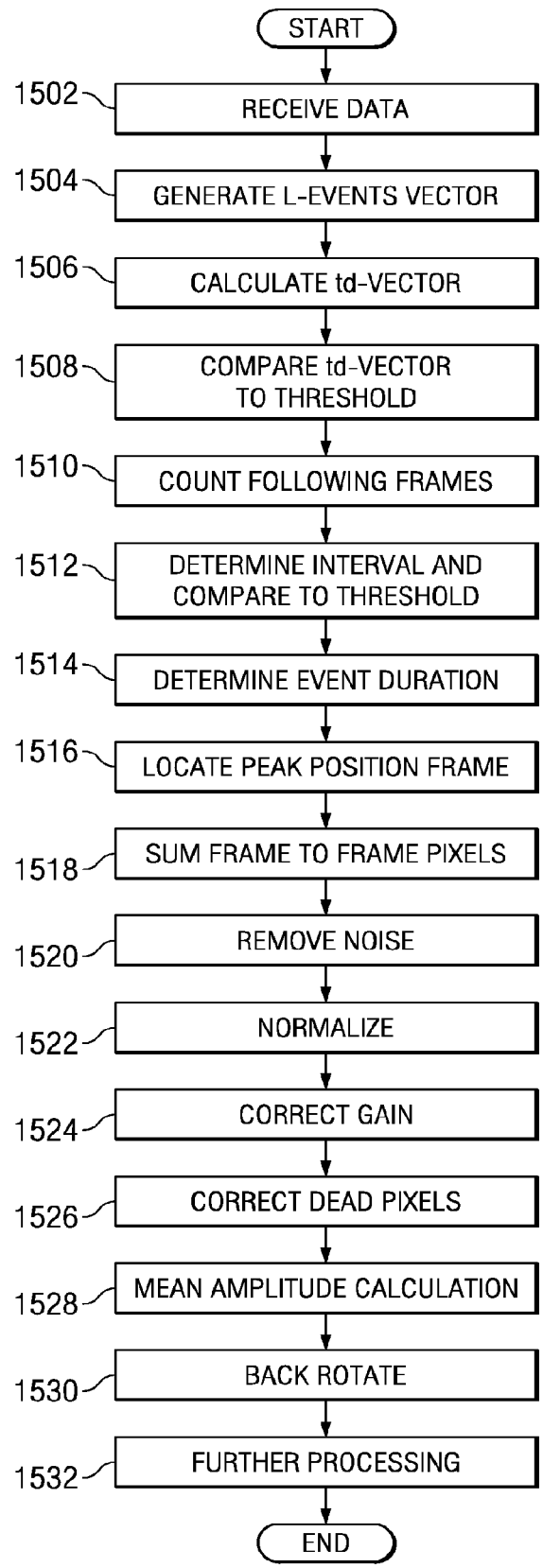
FIG. 15 is a flow chart illustrating an example method of extracting a scattered light signal and particle events from background signals present in data from a detector array in accordance with one embodiment.

FIG. 15 is a flow chart illustrating an example method for extracting scattered light signal and particle events from background signals present in data received from a detector array, such as array 1402. First, in step 1502, the data is received. For example, the data can comprise 20,000 frames (3.4 sec) of 16×16 pixels by 14 bits from 2D-detector array electronics in the form of an array of 256×20,000 double precision values called the rad. In step 1504, each frame is averaged to generate a frame intensity vs. time vector, identified as the L events vector 2106 and shown in FIG. 21. In step 1506, a "tuned-differential" vector (td_vector) is calculated by taking a single frame intensity at time t2 minus 0.5 multiplied by the intensity at time t1 minus 0.5 multiplied by the intensity at time t3. In certain embodiments, background frames are taken on both sides of an event, however, the background may be taken on one side of the event and multiplied by 1.0 instead of 0.5 to determine the tuned differential. In certain embodiments, the event times are on the order of 1 millisecond for the event to pass through the laser in the target zone. During this passage, multiple frames are acquired of the particle, typically from 4 to 20 frames. Times are selected to extract the actual particle event according to flowrate and laser spot size. The entire L vector can be processed in this manner.

In step 1508, events are located by comparing values of the td_vector to a low threshold. The following frames are then counted until the value goes below the low threshold again in step 1510. In step 1512, the maximum intensity in the resulting interval is determined and compared to a high threshold. If the intensity is less than the high threshold, then a possible valid event has occurred. In this case, the duration of the event in number of frames can be determined in step 1514. If the number of frames as determined in step 1514 is greater than a minimum and less than a maximum then a valid event can be indicated. In step 1516, the peak position frame can be determined and placed into a peaks located vector (PLocate).

It will be understood that low threshold, high threshold, minimum and maximum are selected so as to avoid false positives and ensure accuracy. For example, if the low threshold is too low, then many false positives will occur. The high threshold is used to screen out events that are clearly anomalies or not of the desired type. Accordingly, the low and high thresholds must be selected to ensure sufficient sensitivity, while avoiding an abundance of false positives. This will change based on the system and the type of event being detected. Similar considerations much be considered when selecting the minimum and maximum.

In step 1518, for each PLocate position, corresponding frame to frame pixels from the frame before the peak are added with the peak frame and the frame following the peak in the original rad. In step 1520, the following: (0.5 multiplied by the sum of corresponding pixels from the three frames before the peak event and 0.5 multiplied by the sum of corresponding pixels from the three frames after the event) is subtracted from the sum obtained in step 1518 to effectively remove noise from the signal. In the example above, the result is a single event of 256 pixels which can be reshaped to a 16×16 image if so desired. The resulting 16×16 frame can then be normalized by dividing by 3 to generate an event in step 1522. This event is called the extracted signal and represents a valid scattering event to be classified. Each event can be loaded into an array of events starting at index 1.

In step 1524, each pixel in the frame can be corrected for gain, as determined in camera calibration, by multiplying the camera pixel value by its corresponding gain correction factor. This assures even pixel values for uniform illumination. In step 1526, each dead pixel in the frame can be corrected by copying over an adjacent pixel value. Generally, today's camera chips have zero dead pixels, but some may have one or two. In step 1528, for each event frame of 16×16 pixels, a mean amplitude calculation can be performed to generate an amplitude array, followed by a moments calculation on the frame to calculate the rotation of the major and minor axis, followed by elongation. Then, in step 1530, using the rotation angle, each frame can be back rotated to the standard orientation of the major axis horizontally aligned. This will produce an array of events that are all at the standard orientation. In step 1532, the array of events (Events, index), each one representing a frame of 16×16 pixels, can be sent for further preprocessing.

Figure 16:
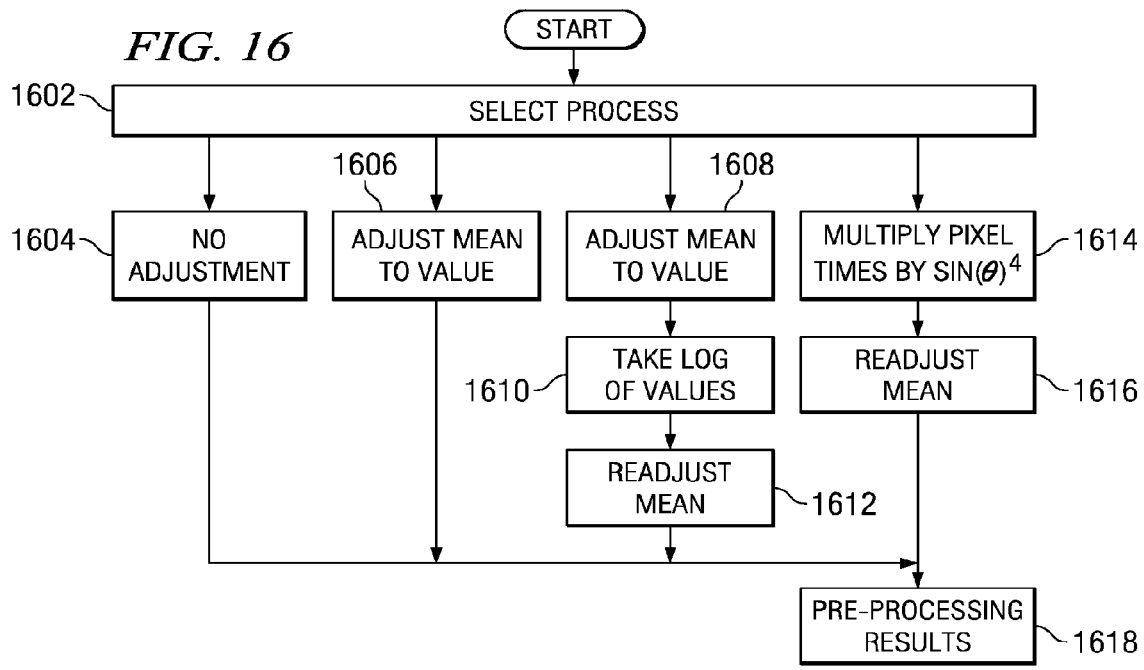
FIG. 16 is a flow chart illustrating example methods of pre-conditioning extracted particle events in preparation for feature extraction in accordance with one embodiment.

FIG. 16 is a flow chart illustrating an example method for pre-conditioning particle events extracted, e.g., using the process of FIG. 15, in preparation for feature extraction. In step 1602, for each frame event in the array of events, one of the following processes can be selected: in step 1604, no amplitude adjustment is made. Alternatively, in step 1606, the mean value is adjusted to 8000, which is called amplitude normalization. The value 8000 is arbitrary and can be any value desired. Alternatively, in step 1608, the mean value is adjusted to 8000, the log of the values is taken in step 1610, and mean is readjusted to 8000 in step 1612. This is called log normal processing. Alternatively, in step 1614, each pixel time is multiplied by sin (scattering angle)^4, and the mean is adjusted to 8000 in step 1616. This is called non-linear processing. In step 1618, results of the pre-processing are produced, which consists of an array of events that have been pre-processed to enhance or suppress amplitude variation. These events can then be sent to frame feature selection process shown in FIG. 17.

Figure 17:
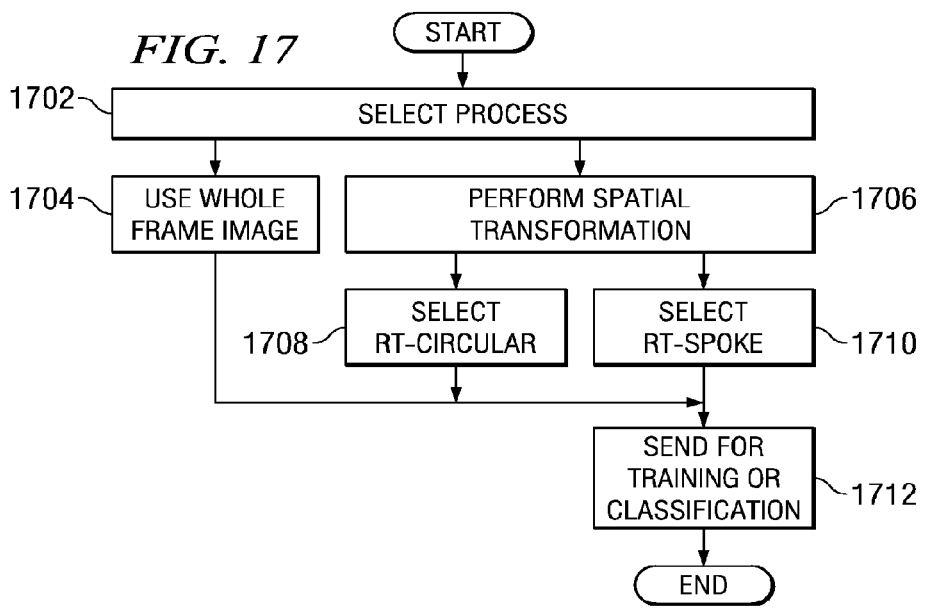
FIG. 17 is a flow chart illustrating example methods used for extracting the feature signals in accordance with one embodiment.

FIG. 17 is a flow chart illustrating an example method for extracting event features for recognition and later classifying of particle events. In step 1702, for each frame event in the array of events, one of the following processes can be selected: in step 1704, the whole frame image can be used with no additional processing required. Alternatively, in step 1706, a spatial transformation can be performed on the frame, changing the 16×16 image that is symmetric about the center scattering angle of zero degrees into an image that represents Radial and Angular values (R-Theta transformation). The R-Theta image typically has 18 radial vectors, with each radial vector containing 8 values representing 8 scattering angles about the center of the scattering plane. In this example, the transform is represented by an array of 8×18 values or 18×8 values depending of which orientation is required for further processing. RT-circular, or RT-spoke data can then be selected in steps 1708 and 1710 respectively for further processing. In step 1712, the frame based features can be sent for either training or classification as described below.

Figure 18:
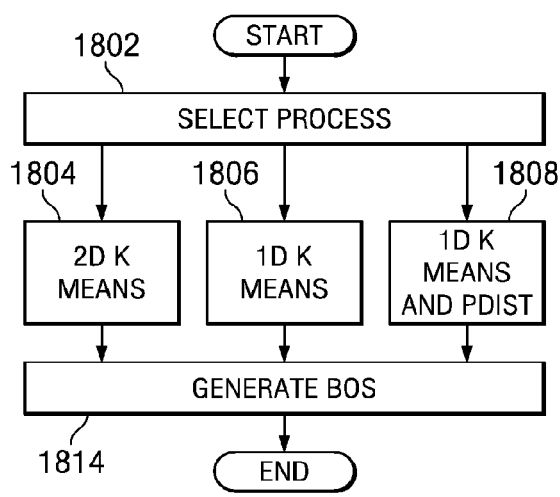
FIG. 18 is a flow chart illustrating an example method of training a particle detection system to recognize and later classify particle events in accordance with one embodiment.

FIG. 18 is a flow chart, illustrating an example method for training a particle detection system to generate a Biological Optical Signal (BOS) for classifying particle events in accordance with one embodiment. For each extracted feature event that is going to be used for training the system, one of the following training methods can be selected in step 1802: in step 1804, two-dimensional (2D) kmeans and correlation coefficient can be used. Alternatively, in step 1806, one dimensional (1D) kmeans and correlation coefficient 1806 can be used. Alternatively, in step 1808, 1D-kmeans and pdist can be used. Pdist is measure of how close a given vector is to another in kmeans and is defined in Matlab documentation. The input parameters to these training methods include the number of vectors for classification, typically 4 to 32 vectors, the minimum correlation percentage, typically 80% to 98%, the pdist threshold, typically 80 to 120, and whether to send species separately or not. In certain embodiments, a separate vector generation for each species under training is used. For example, background water is generally called matrix and is sent through training separate from a measured species such as *E.coli*.

After going through vector generation using kmeans, the results are quality verified by measuring the correlation coefficient between the training vectors and the kmeans vectors, or a calculated distance between the training vectors to the nearest kmeans vector using pdist. The trained vectors are tagged as to which species they correspond to and placed into a Bio-Optical Signature (BOS) along with the set of parameters, and used in real-time running of the system. In real-time running of the trained system, FIG. 19, the detected feature extracted events from FIG. 17 are compared to the trained vectors generated in accordance with the process of FIG. 18 in order to classify the event.

Figure 19:
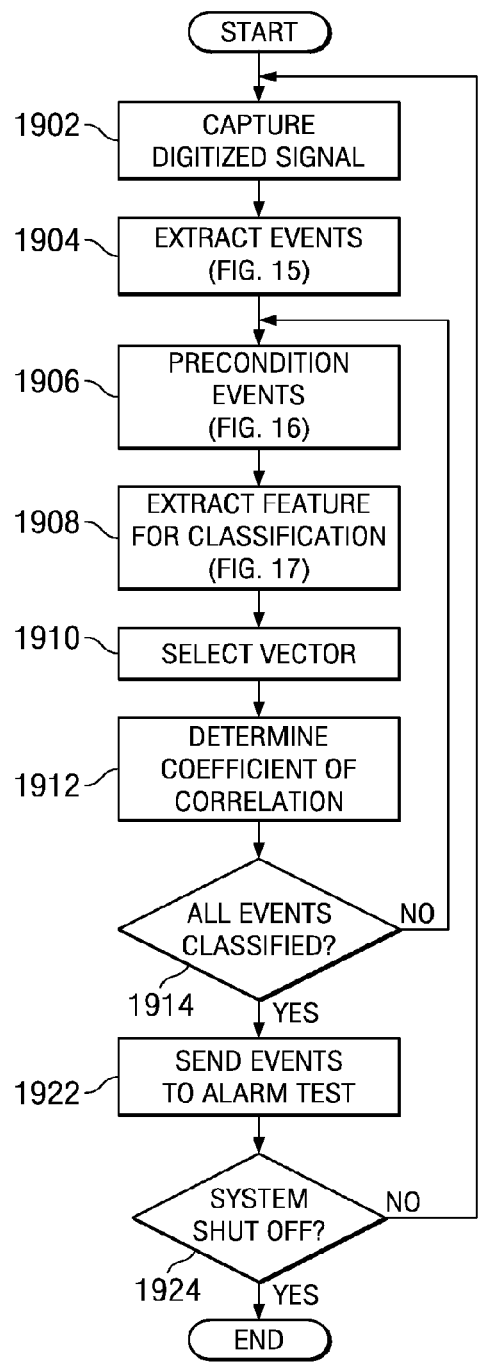
FIG. 19 is a flow chart illustrating an example method for operating system for classifying particle events in accordance with one embodiment.

FIG. 19 is a flow chart illustrating an example method for classifying particle events in realtime in accordance with one embodiment. In step 1902, digitized signals from a detector are captured, e.g., from camera 1400 of FIG. 14. The events of interest can then be extracted, in step 1904, from the raw data, e.g., using the methods of FIG. 15. Each event can then be precondition in step 1906, e.g., using one of the methods of FIG. 16. In step 1908, the feature to be used in classification can be extracted to generate a feature vector, e.g, in accordance with the method of FIG. 17. In step 1910, for each feature vector, the feature vector can be compared against each trained vector in the BOS, e.g., produced using the methods of FIG. 18. The vector in the BOS that has the highest correlation when the system was previously trained, e.g., using either method 1804 or 1806 or the smallest pdist if the system was previously trained using 1808, can then be selected in step 1912. The possible classification can then be identified by selecting a tagged species identification corresponding to the selected vector.

In step 1912, for each event, if the coefficient of correlation calculated between the selected vector for the event is equal to or higher than the minimum correlation percentage for the previously trained BOS, using either steps 1804 or 1806, then the event can be classified as the species tagged corresponding to the selected vector. Alternatively, if the system was previously trained using method 1808, and if the pdist is less than or equal to the pdist threshold, then the event can be classified as the species tagged corresponding to the selected vector. If in either case the threshold tests are not satisfied, then classify the event as unknown.

In step 1914, steps 1906 through 1912 can be repeated until all the events have been classified, generating a count of events vs. species result. In step 1922, the classified results can be sent to the alarm test process illustrated in FIG. 20. In step 1924, steps 1902 through 1922 can be repeated until the system is shut off or the program is ended.

Figure 20:
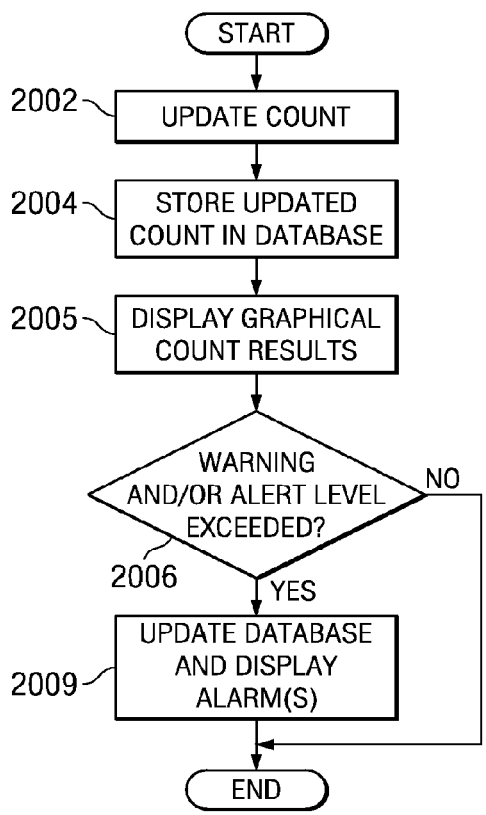
FIG. 20 is a flow chart illustrating example alarm and warning methods that can be implemented in a particle detection system in accordance with one embodiment.

FIG. 20 is a flow chart illustrating an example alarm and warning process in accordance with one embodiment. In step 2002, for each set of classified results and for each species within the results, the counts in each species are added to a species count vs. time record database within computer memory storage. In step 2004, the database receives the new count vs. species information and is updated. In step 2005, the count result can be displayed, e.g., via a graphical display. In step 2006, for each species, the results of step 2004 are examined to determine if the corresponding count rate exceeds certain warning levels or alert levels. For example, there can be individual levels for each species in the BOS and for "unknowns". In step 2009, if any warning or alert level is exceeded for any of the species in the BOS, or for the "unknowns" then a corresponding entry in the database can be created and the results displayed on a user graphical interface. Additionally, the warnings and alerts may be sent to external SCADA or computer systems used for operations monitoring. The system can be programmed to automatically divert the sample outflow from the target zone, which normally may go to a drain, to a sample bottle or to an external sample collecting filter for further analysis by the user.

Figure 21A:
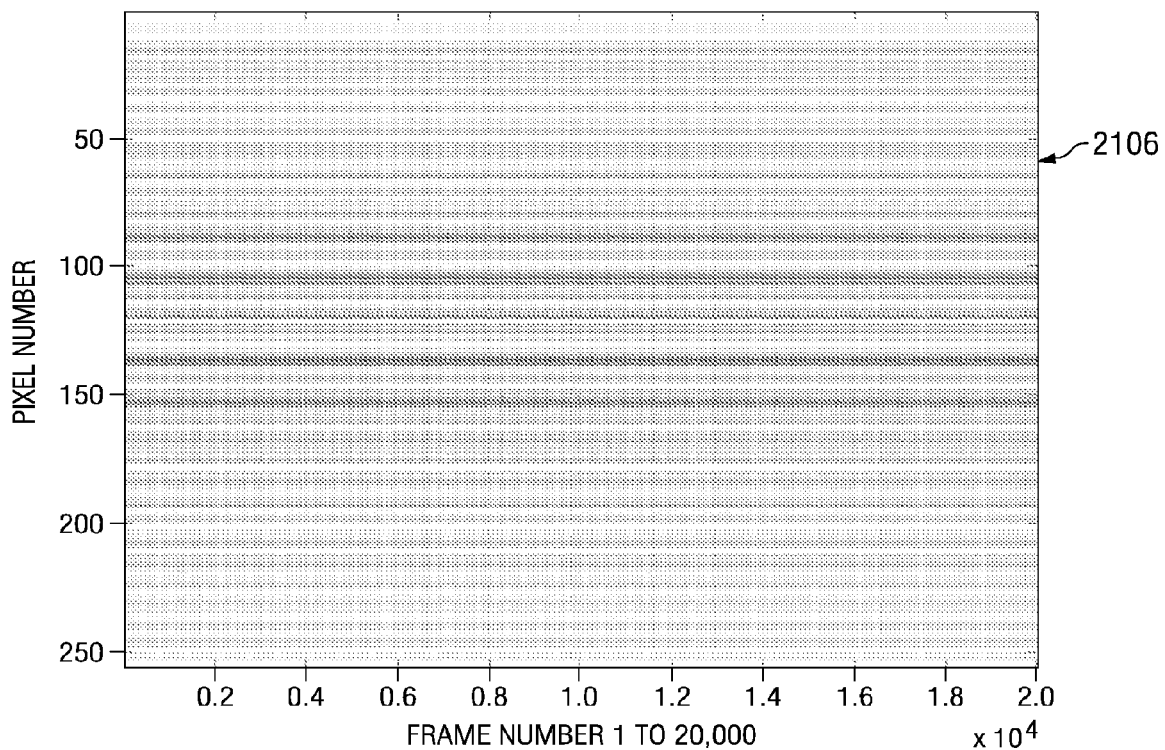
FIG. 21A illustrates one rad comprising 256 pixels in each frame and 20,000 frames representing elapsed time showing some *E.coli* events in Filtered Lab Water detected using a particle detection system in accordance with one embodiment.

FIG. 21A illustrates one rad 2106 comprising 256 pixels in each frame and 20,000 frames representing elapsed time of approximately 3.4 seconds, showing some *E.coli* events in filtered lab water. The *E.coli* events are not easily seen in the raw data of the rad.

Figure 21B:
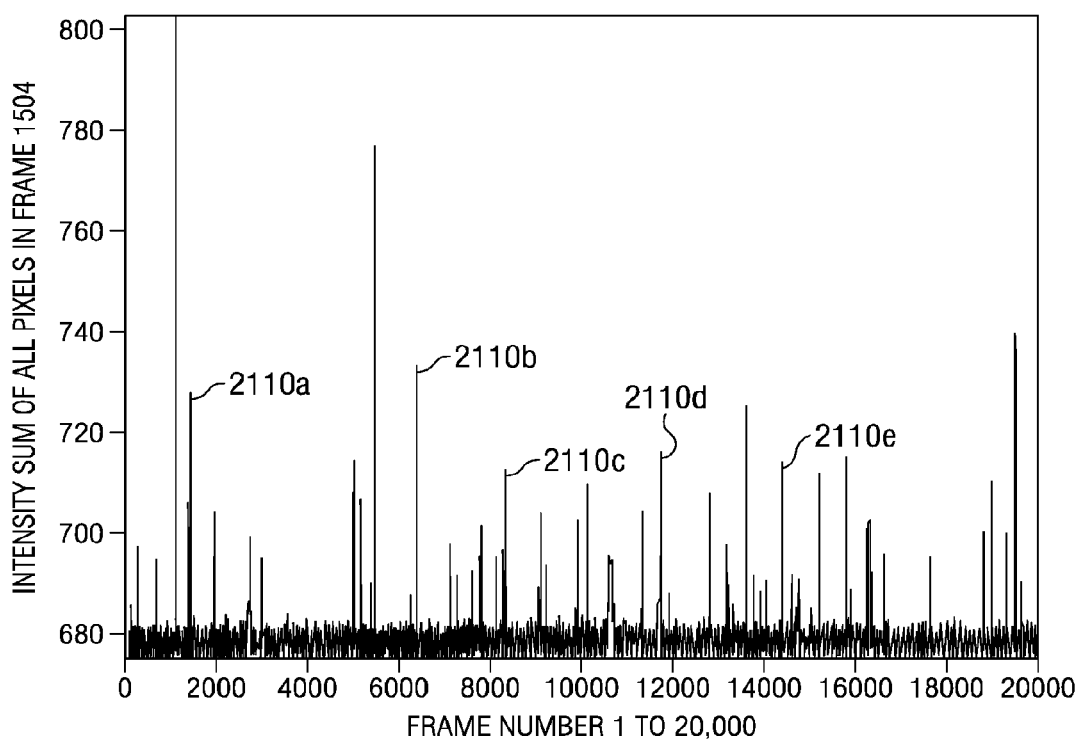
FIG. 21B illustrates the rad of FIG. 21A where the 256 pixels in each frame are summed and represented frame average signal vs. time.

FIG. 21B illustrates rad 2106 of FIG. 21A where the 256 pixels in each frame are summed and represented as a frame average signal vs. time. The *E.coli* events are clearly seen in the data and several are pointed out 2110*a-e*. There are approximately 43 events that are shown in the figure and that will be extracted by later processing.

Figure 22:
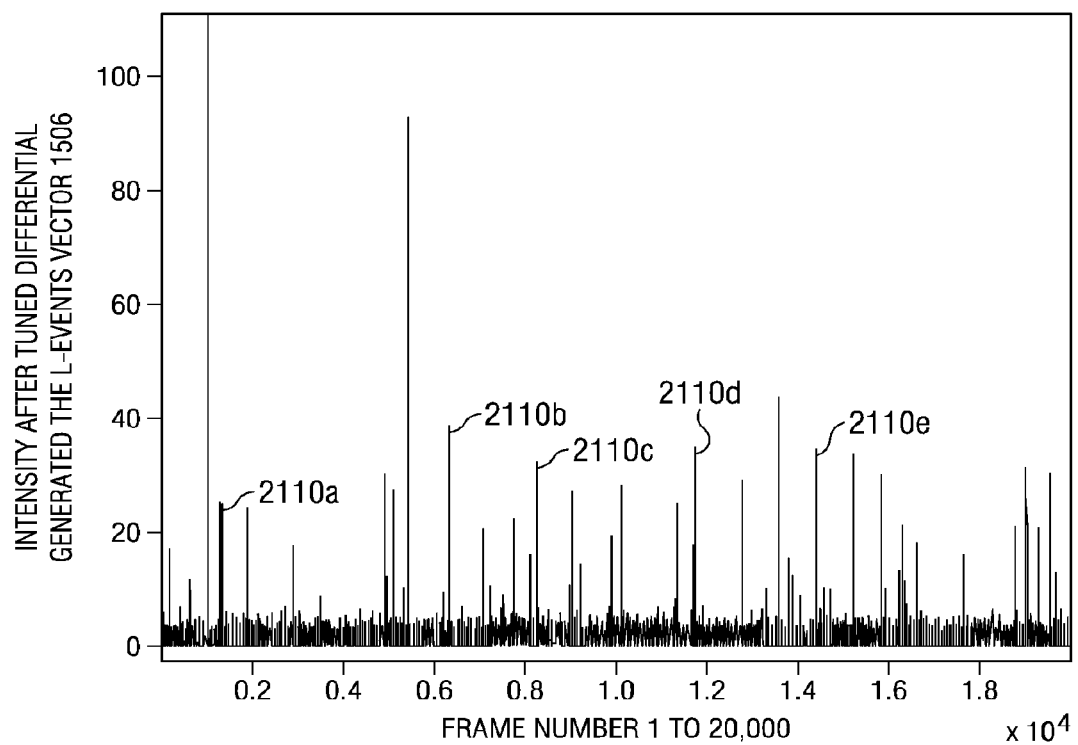
FIG. 22 illustrates an example L-events vector using tuned-differential signal vs. time.

FIG. 22 illustrates the L-events vector using tuned-differential signal vs. time, showing the same E.coli events as in FIG. 21B, 2110*a-e*.

Figure 23:
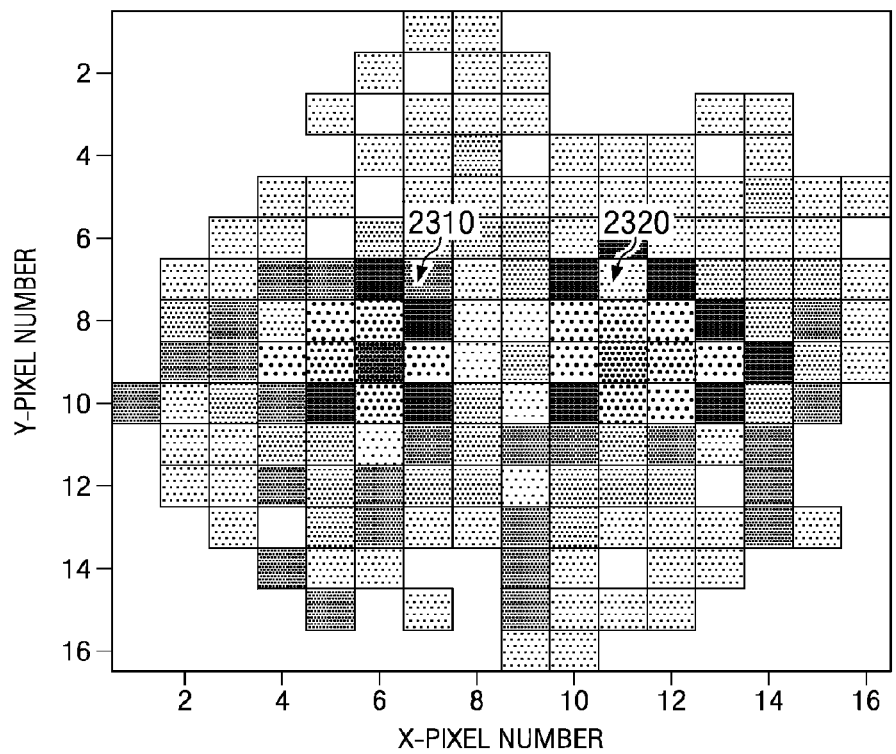
FIG. 23 illustrates one extracted signal representative of *E.coli*.

FIG. 23 illustrates one extracted signal from peak 2110*b* representative of *E.coli*. The frame of 256 pixels has been displayed as an image of 16 pixels by 16 pixels representative of the actual pixels, e.g., on detector 1402 of FIG. 14 and detector 2710 of FIG. 27. The displayed intensity of each pixel is such that the darkest areas in FIG. 23 correspond to the pixels that have the most photons collected or the highest intensity. The clear area in the center of the image is a result of, e.g., beam-stop 110 of FIG. 1 or 1006 in FIG. 11, or prism 1306 in FIG. 13, blocking the lowest angles of scatter and the primary beam. The rod-shape that is typical of *E.coli* and many other bacteria is evident in the image shown as the horizontal area of brightness. This image has been rotated 1506 such that its major axis is horizontal. Two bright areas 2310 and 2320 are representative of the light pattern from the *E.coli*

Figure 24:
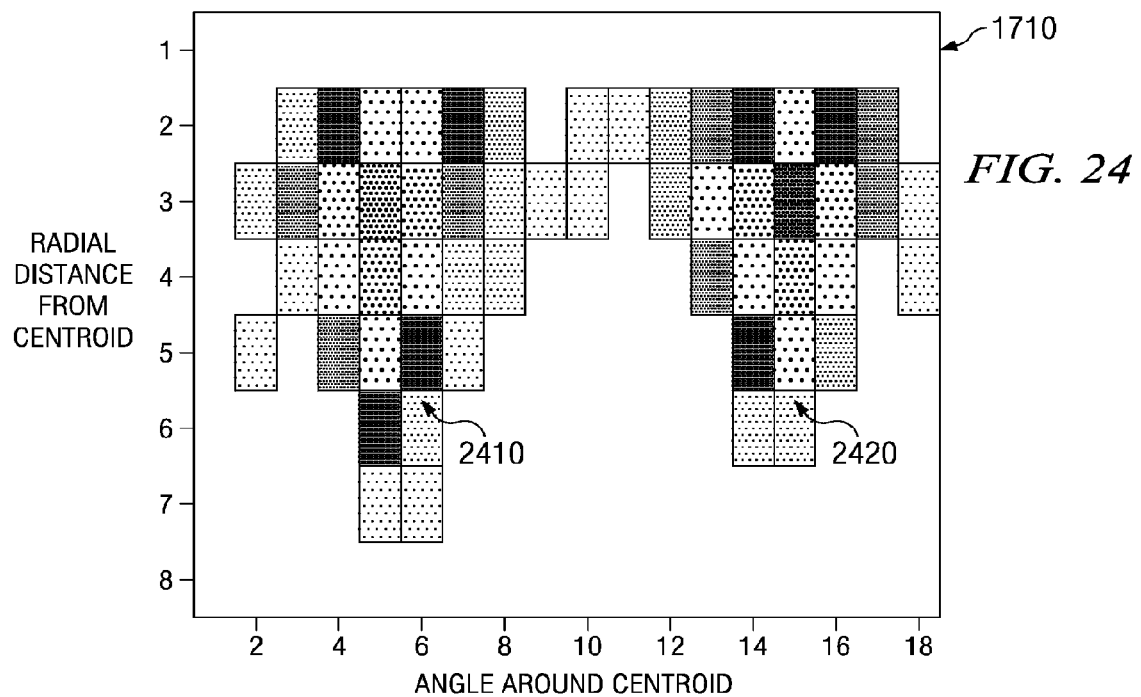
FIG. 24 illustrates the Radial_Theta transform of the *E.coli* signal of FIG. 23.

FIG. 24 illustrates the Radial_Theta circular transform of the *E.coli* signal of FIG. 23. Here the same two bright spots 2410 and 2420 are transformed into the corresponding bright spots 2410 and 2420 respectively.

Figure 25:
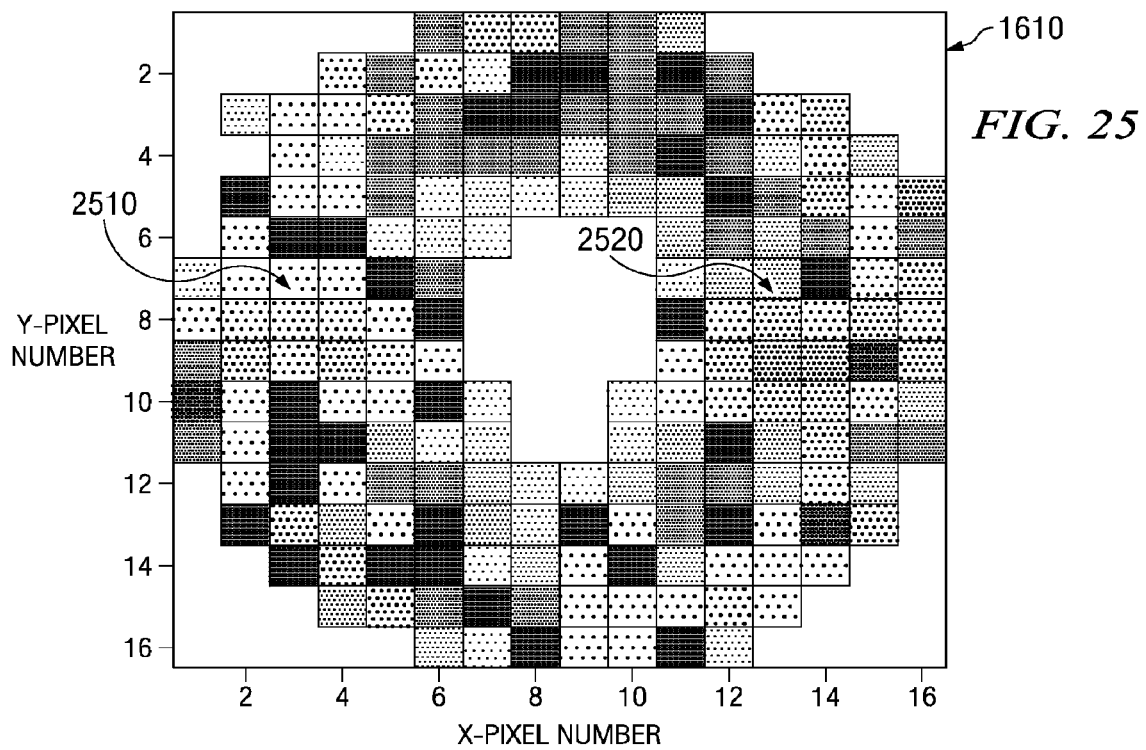
FIG. 25 shows the effects of the Non-linear processing on the representative signal shown in FIG. 23.

FIG. 25 shows the effects of Non-linear processing described in relation to FIG. 6 above, on the representative signal shown in FIG. 23. In certain embodiments, the non-linear processing multiplies each pixel intensity value times sin(scattering angle)^4 and then re-normalize. The power 4 is preferred, however, any power between 0.5 and 8 may be utilized. The same two bright spots 2410 and 2420 are moved away from the center and form areas 2510 and 2520 respectively and their relative intensity to the other pixels in the image is somewhat diminished.

Figure 26:
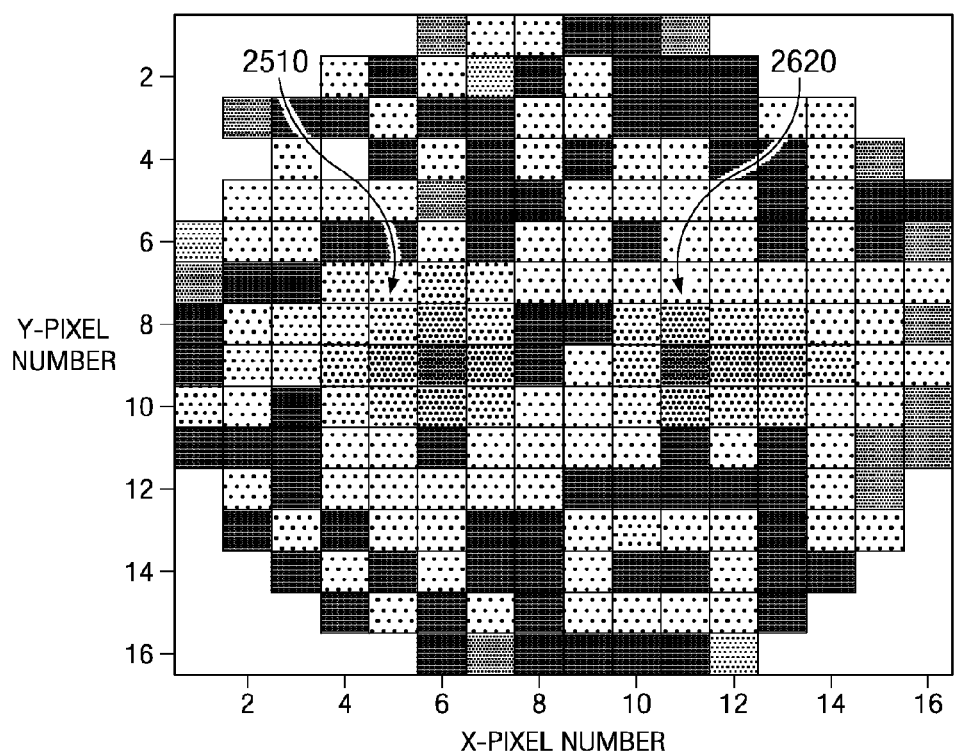
FIG. 26 shows the effects of the Log-normal processing on the representative signal shown in FIG. 23.

FIG. 26 shows the effects of the Log-normal processing on the representative signal shown in FIG. 23. The same two bright spots 2410 and 2420 are shown as 2610 and 2620 respectively and their relative intensity to the other pixels in the image is greatly diminished.

Figure 27A:
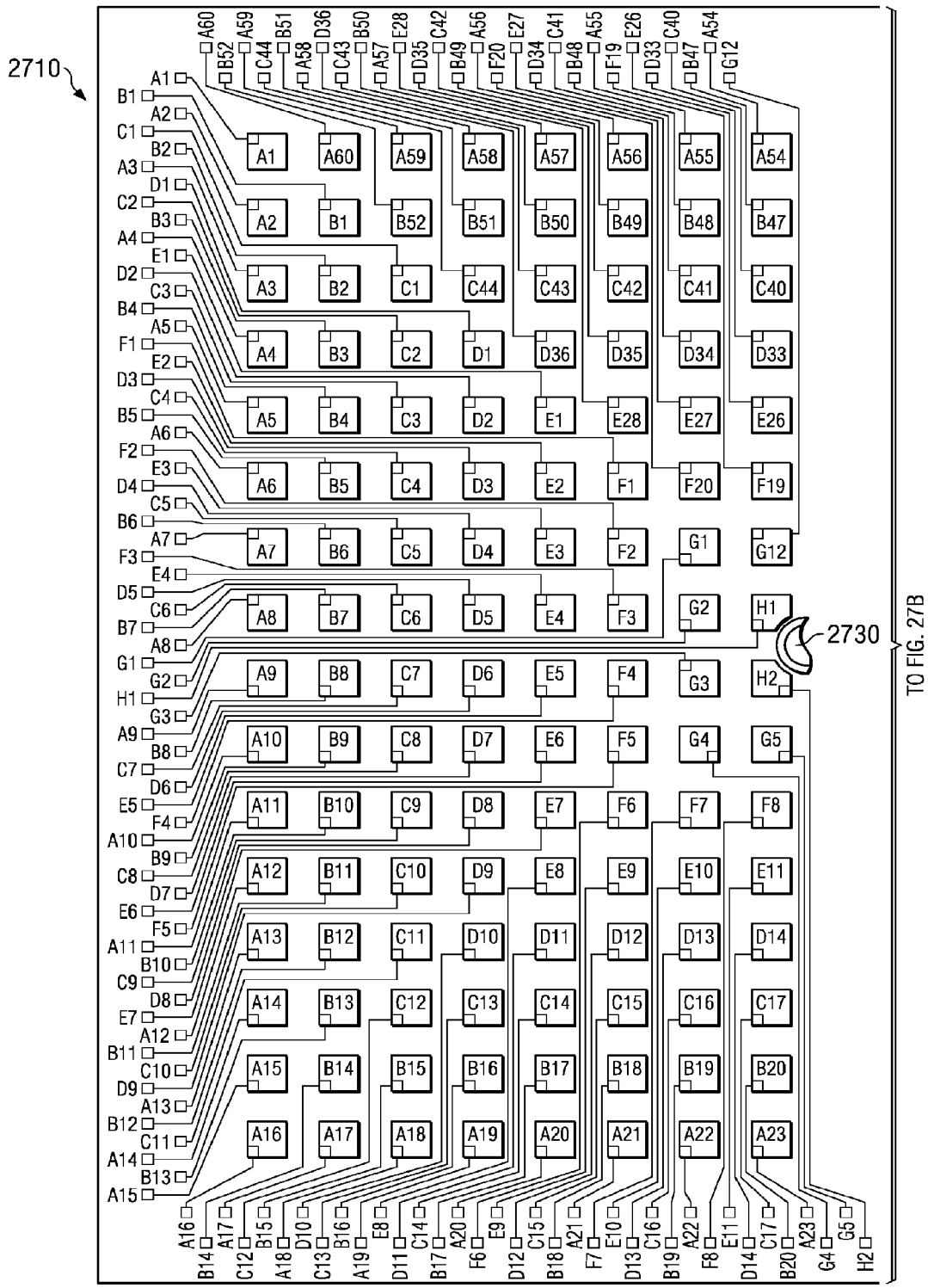
FIG. 27 illustrates an example 256 pixel sensor in accordance with one embodiment.
Figure 27B:
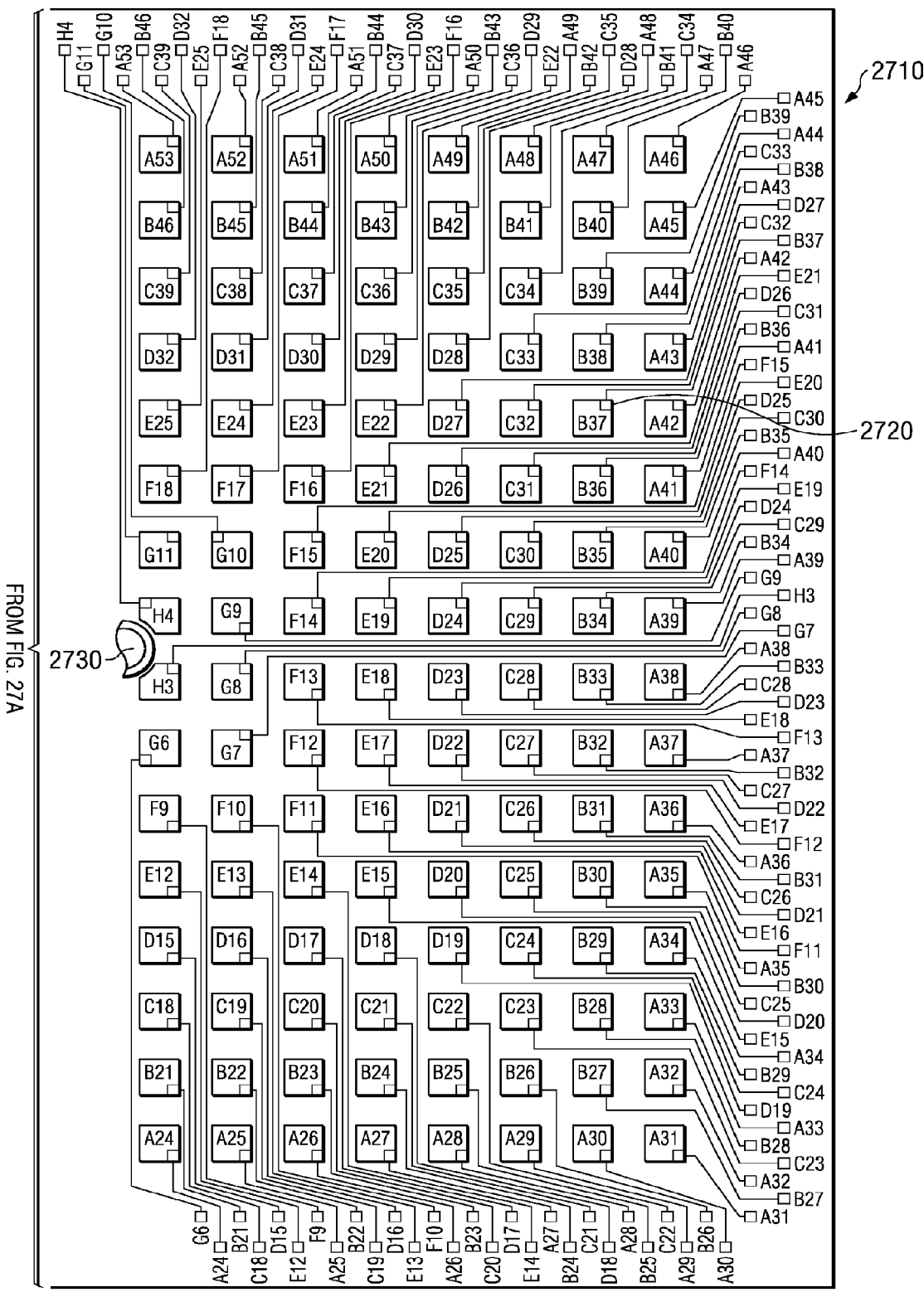

FIG. 27 illustrates one embodiment of a 256 pixel sensor 2710, that can be used in accordance with the systems and methods described herein. Reference 2720 identifies pixel B37 on sensor 2710. This pixel is also identified by x=15 y=5 in a 16×16 pixel configuration. Reference 2730 identifies a center location on sensor 2710 wherein all material has been removed forming a through-hole. This area would allow the primary laser beam to transit sensor 2700 from either the front photon-sensitive side or the rear. Note that the pixels H1 through H4 have had some material removed to make room for the through-hole feature. The pixel size is approximately 1.1 millimeter square and the pixels are spaced on approximately 1.5 millimeter centers. This relatively large pixel area detector allows for sensitive light measurements. In certain embodiments, construction of sensor 2710 is of a silicon photodiode array, however a CCD array, CMOS array, or a CID array could also be used. The benefits of a Photodiode array are that it has a superior signal dynamic range compared to a CCD, CMOS, or CID device.

FIG. 28 shows representative images from a 2, 4, and 8 micron diameter polystyrene spheres, from *Cryptosporidium*, dirt, *Giardia*, and *E.coli* where white is the brightest part of the image or most scattered photons. These images were taken with a 320 pixel by 240 pixel CMOS array camera. These images were not rotated to principle axis horizontal but were captured as the particle transited the laser beam. Each image has been normalized to intensity, otherwise the *E.coli* image would be the dimmest and the 8 micron sphere the brightest.

Figure 29:
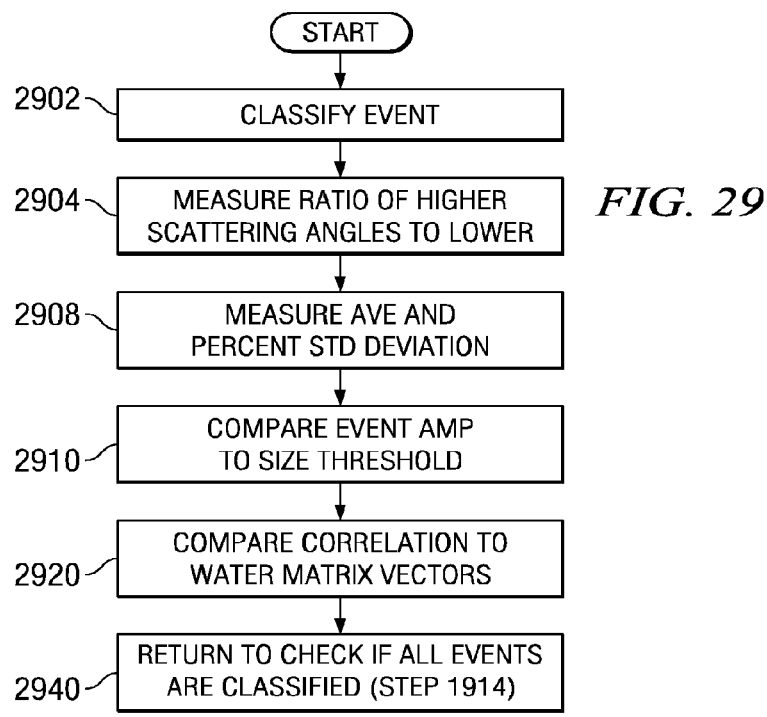
FIG. 29 is a flow chart illustrating an example method for additional qualification or classification steps that can be used to help minimize any false positives in accordance with one embodiment.

FIG. 29 is a flow chart illustrating an example method for additional qualification or classification steps that can be used to help minimize any false positives produced when implementing the process of FIG. 19. These steps can be performed in addition to, or in place of certain steps illustrated in FIG. 19, e.g., after an event has been classified, e.g., in step 1912 and before step 1914. First, in step 2902 four (4) additional qualifiers can be evaluated if the event has been classified as anything other than "unknown."

Figure 30:
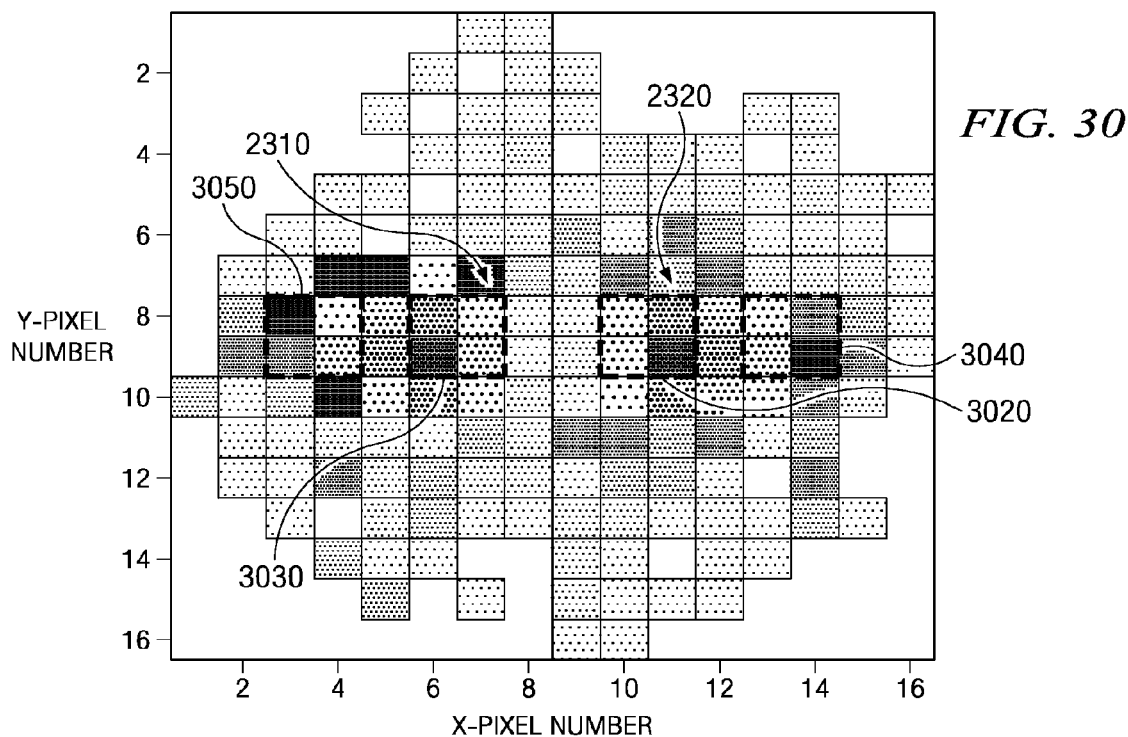
FIG. 30 illustrates how a ratio can be produced between the higher scattering angles and lower scatter angles for the *E.coli* signal of FIG. 23.

In step 2904, the fist of these qualifiers can be used if the event has been classified as a rod-shaped bacteria, such as *E.coli*. This step entails measuring the ratio of the higher scattering angles to the lower scattering angles. With reference to FIG. 30, this can be accomplished using a camera by summing the two outer pixel areas shown by boxes 3040 and 3050 and dividing by the sum of the pixels in the inner areas identified by boxes 3020 and 3030 to produce a ratio. If, for example, the ratio is between 0.2 and 0.5, then the classification can be left as previously determined; however, if the ratio is otherwise, then the event can be re-classified as "unknown."

Figure 31:
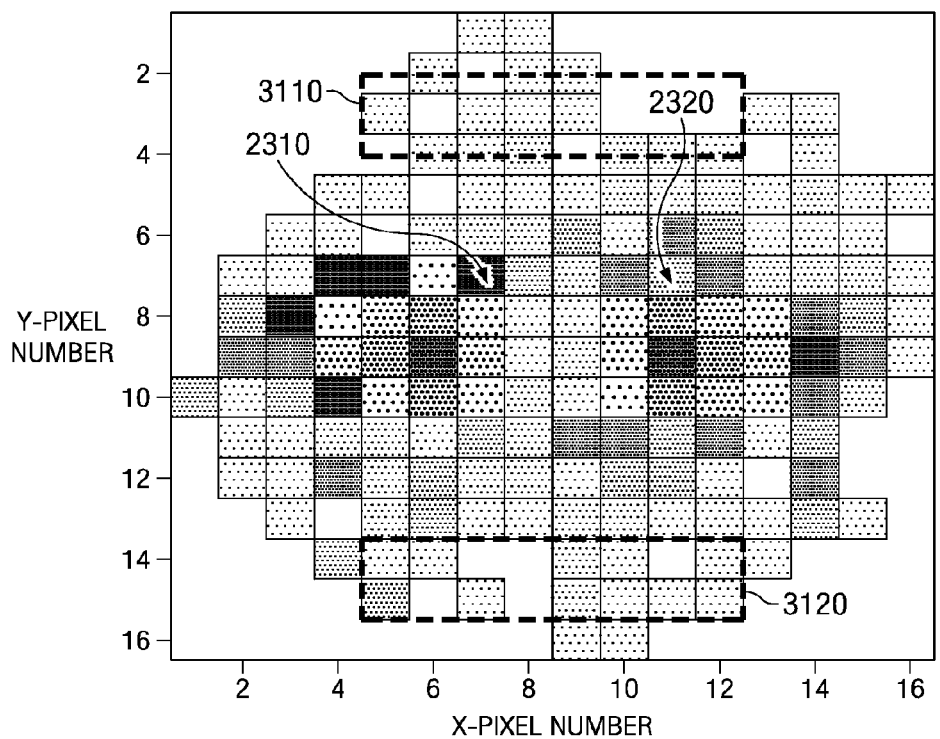
FIG. 31 illustrates how a percent standard derivative can be produced for the pixels comprising the *E.coli* signal of FIG. 23.

In step 2908, the second qualifier can be used if the event has been classified as a rod-shaped bacteria, such as *E.coli*. This step entails measuring the average and the percent standard deviation of the pixels in boxes 3110 and 3120 as shown in FIG. 31. If the Percent Standard deviation is above a threshold, then the event can be re-classify as "unknown."

In step 2910, the third qualifier can be used if the event has been classified as a small organism typical of rod-shaped bacteria, such as *E.coli,* or spores such as *B. subtilis*. Here a comparison of the event amplitude as measured in step 1516 to a size threshold can be made and if the amplitude is larger than the threshold, then the event can be re-classified as "unknown." Otherwise, the event classification can be left as before. If the event has been classified as a large organism typical of *Cryptosporidium, Giardia,* or a Yeast, then the event amplitude as measured in step 1516 can be compared to a size threshold, and if the amplitude is less than the threshold, then the event can be re-classify as "unknown." Otherwise the classification can be left as before.

In step 2920, the fourth classifier can be used. Here the actual correlation measured in step 1912 can be compared against each of the correlations to the vectors representing a water matrix, and if the difference from the nearest water vector is not greater than a threshold, then the event can be re-classified as "unknown."

Each of the four additional qualifiers or further classifications shown in FIG. 29 can be used to improve the overall quality of the initial classification and to reduce any false positives that the system may experience in some applications.

Finally in step 2940 the analysis is returned to step 1914 in FIG. 19.

Figure 32:
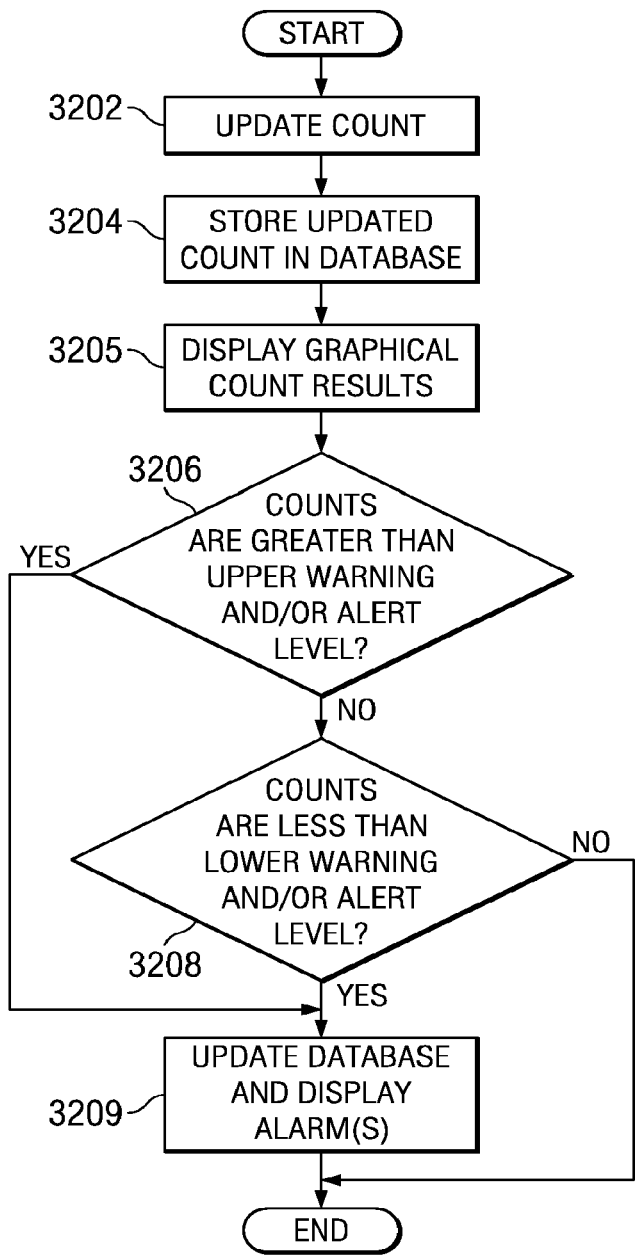
FIG. 32 is a flow chart illustrating chemical alarm and warning methods that can be implemented in a particle detection system in accordance with one embodiment.

FIG. 32 is a flow chart illustrating an example alarm and warning process in accordance with one embodiment where the conditions tested are for possible biological and/or toxin attacks. In step 3202, for each set of classified results and for each species within the results, the counts in each species are added to a species count vs. time record database within computer memory storage. When testing for chemical toxin, biotoxin, or radiation toxic agents (CBR attack), at least one of the species should be a naturally occurring species selected to monitor for a possible toxin attack. In step 3204, the database receives the new count vs. species information and is updated. In step 3205, the count result can be displayed, e.g., via a graphical display. In step 3206, for each species, the results of step 3204 are examined to determine if the corresponding count rate exceeds certain warning levels or alert levels. For example, there can be individual levels for each species in the BOS and for the particles classified as "unknowns."

In step 3208, for the naturally occurring species chosen to be the toxin monitoring species, the results of step 3204 are examined to determine if the corresponding count rate falls below the expected normal rate and is less than certain warning levels or alert levels corresponding to a possible toxin attack. For example, there can be individual levels for each normally occurring species in the BOS and for the normally occurring "unknowns." In step 3209, if any warning or alert level for either a potential biological attack is exceeded, or for a toxin attack is less than, for any of the corresponding species in the BOS, or for the "unknowns" then a corresponding entry in the database can be created and the results displayed on a user graphical interface. Additionally, the warnings and alerts may be sent to external SCADA or computer systems used for operations monitoring. The system can be programmed to automatically divert the sample outflow from the target zone, which normally may go to a drain, to a sample bottle or to an external sample collecting filter for further analysis by the user.

Figure 33:
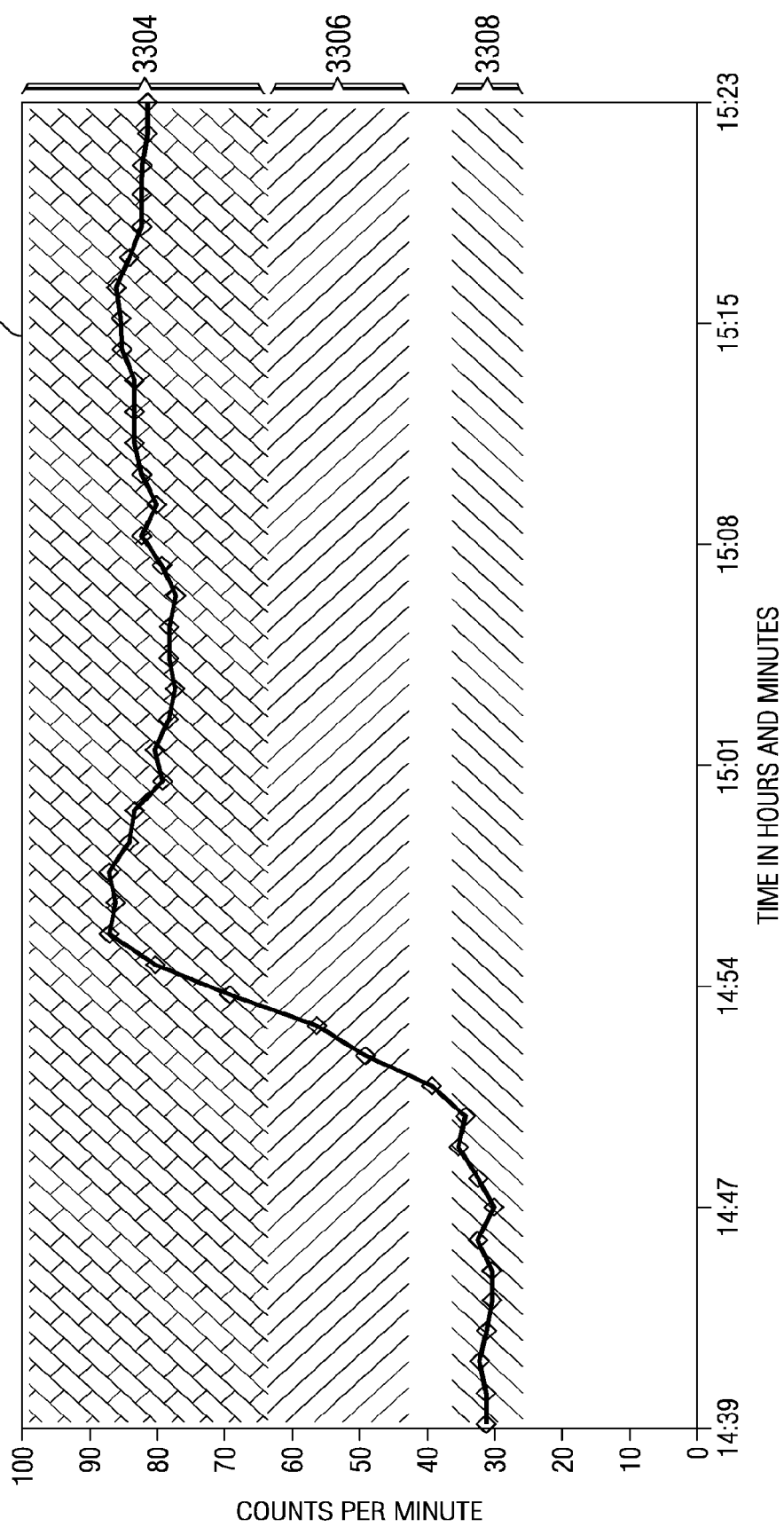
FIG. 33 is a graph illustrating the results of a spike test of *B. subtilis* into tap water simulating a possible biological attack of Anthrax spores.

FIG. 33 is a graph 3302 illustrating the results of a spike test of *B. subtilis* at a concentration of 200 organisms per milliliter in Rancho Bernardo (a San Diego Suburb) tap water, showing an average background of about 31 counts per minute before the spike and 81.9 counts per minute afterwards. The normal operating background of Rancho Bernardo tap water is shown on the graph as 3308, the warning level 3306, and the alert level 3304 are also shown as various hatched areas on the graph background. *B. subtilis* is the Environmental Protection Agency recommended surrogate for *B. anthracis* (anthrax spores) for use in testing. The graph shows that in less than 10 minutes elapsed time the system went from normal to warning to alert level.

Figure 34:
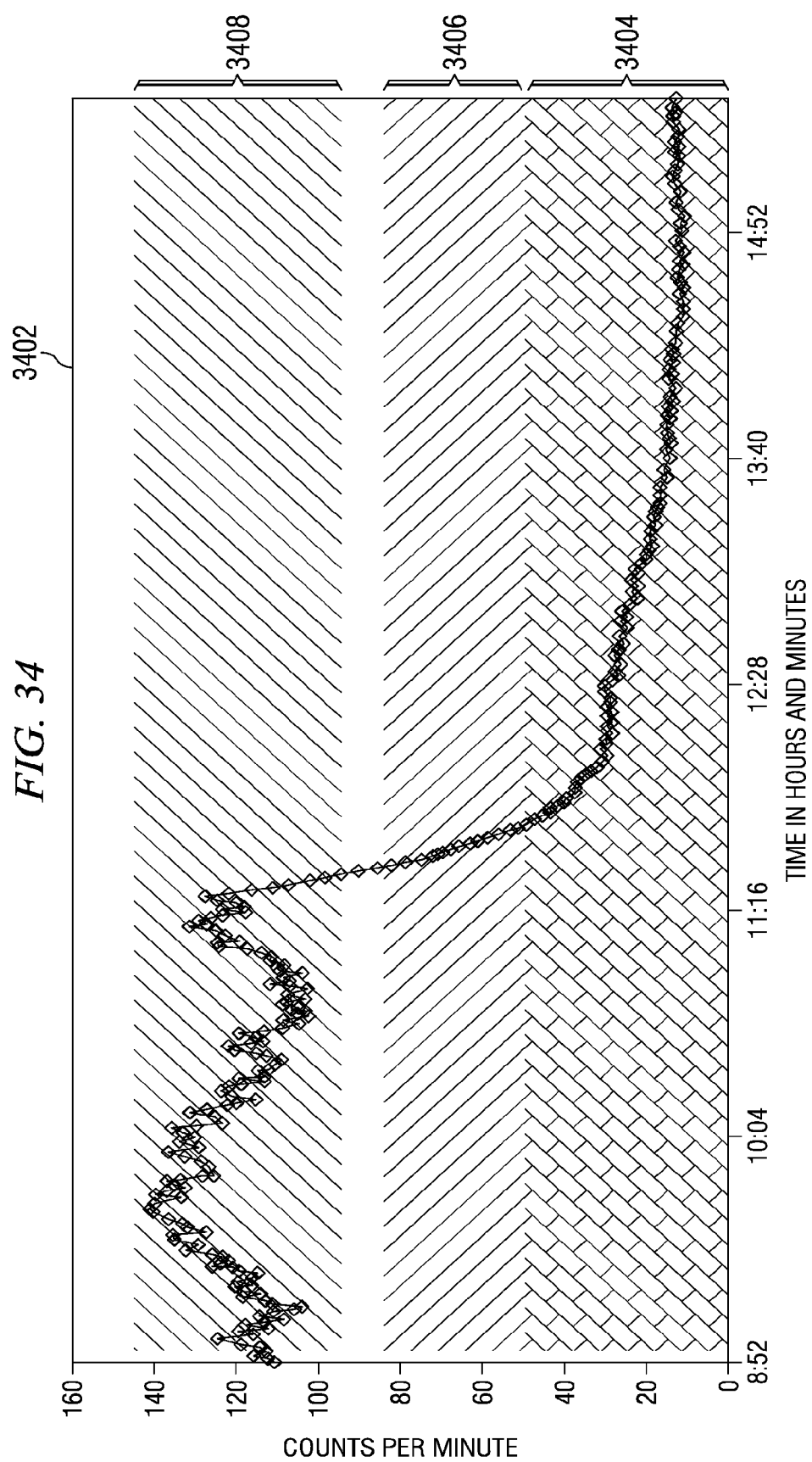
FIG. 34 is a graph illustrating a decrease in natural occurring bacteria representing a possible undesirable toxic chemical being introduced into the monitored water.

FIG. 34 is a graph 3402 illustrating the results of a spike test conducted in Rancho Bernardo tap water to test the system for monitoring for possible undesirable toxins being introduced into the water. Normally occurring rod-shaped bacteria were trained into the BOS and monitored, showing an average background of about 120 counts per minute before the spike of Sodium Hydroxide (NaOH) in quantity to produce 0.1 normal NaOH. The results of the spike begin to show in the counts per minute at 11:20 AM which fall to 10 counts per minute in a little over an hour.

The normal operating background of Rancho Bernardo tap water for the normally occurring rod-shaped bacteria is shown on the graph as 3408, the warning level 3406, and the alert level 3404 are also shown as various hatched areas on the graph background. The graph shows that in about 30 minutes elapsed time the system went from normal to warning to alert level. The reason for this behavior of the counts per minute in normally occurring rod-shaped bacteria in tap water as a toxic agent is added is that the bacteria are affected by the toxic agent and as a result change their morphology and general shape. This change in shape causes the system to detect fewer rod-shaped bacteria per minute as the toxic agent takes effect. Example naturally occurring water borne bacteria that may be used in the systems and methods described herein can include species within the genera *Pseudomonas, Aeromonas, Alcaligenes, Acinetobacter, Klebsiella, Flavobacterium, Chromobacterium*, and many others. The systems and methods described herein are not limited to using rod-shaped bacteria as the health monitor for detection of a toxic agent introduced into the water. Toxic agents that may be detectable by the present invention but not limited to include Cycloheximide, Sodium Arsenate, Sodium Fluoroacetate, NaOH, KOH, acids; Biotoxins such as botulism; or a range of radiation emitting elements or compounds that emit alpha, beta, and or gamma radiation throughout the water;

and other toxins in sufficient quantities to affect the normal bacteria count rate either by directly destroying the bacteria morphology or by damaging the biofilm that may be present in the water system and thereby reducing the count rate The following examples illustrated results produced using the systems and methods described herein.

EXAMPLE 1

A Bio-Optical Signature (BOS) was generated for the spores *B. subtilis* and for the protozoan *Cryptosporidium*. Normal tap water from Rancho Bernardo in San Diego County was caused to flow through the system in the normal manner and the system run normally. The one (1) minute count rate for Unknown was 1341 counts per minute and for the *B. subtilis* species vectors was 40±6 counts per minute. A spike of *B. subtilis* containing solution was injected into the water flow at a concentration of 750 *B.subtilis* organisms per milliliter. For the vectors identifying *B.subtilis* the count rate increased from 40 to 117 counts per minute, clearly showing that *B. subtilis* was detected at 750 organisms per milliliter. A minimum level of detection was calculated at 522 organism per milliliter. The unknown count rate went from 1341 counts per minute to 1403 counts per minute.

EXAMPLE 2

A Bio-Optical Signature (BOS) was generated for the spores *B. subtilis* and for the protozoan *Cryptosporidium* (Crypto). Normal tap water from Rancho Bernardo in San Diego County was caused to flow through the system in the normal manner and the system run normally. The one (1) minute count rate for Unknown was 1521 counts per minute and for the Crypto species vectors was 57±11 counts per minute. A spike of Crypto containing solution was injected into the water flow at a concentration of 2000 organisms per milliliter. For the vectors identifying Crypto the count rate increased from 57 to 165 counts per minute, clearly showing that Crypto was detected at 2000 organisms per milliliter. A minimum level of detection was calculated to be 337 organisms per milliliter. The unknown count rate went from 1521 counts per minute to 1768 counts per minute.

EXAMPLE 3

Testing of *E.coli* in Bernardo Tap water and in Filtered (to 0.2 micron) Lab water indicates that the minimum levels of detection are 8000 organisms per milliliter in tap water and 24 organisms per milliliter in Filtered Lab water. This indicates that for the smaller species and to some extent larger species, the limit of detection is a function of not only the equipment design but also the normal level of bacteria or other interferences in the water. In the Bernardo Tap Water a significant number of Heterotrophic Plate Count bacteria and other naturally occurring bacteria are present and affect the minimum levels of extra bacteria that the system can detect. Generally, the background count rate and standard deviation of the count is used in part to calculate minimum detection levels. To be detectable, the extra bacteria have to provide a count rate that is statistically above the count rate from the normal background at either 1 sigma, 3 sigma, or 6 sigma above the background count rate, depending on how the user wants to operate the system.

The naturally occurring bacteria present in the water system also provide a source and signal to monitor for undesirable toxins being introduced into the water, as they are stressed by harmful toxins, their number, morphology, and shape change, resulting in a decrease in the normal counts per minute in the monitored bacteria. Similar to the discussion above, the background count rate and standard deviation of the count is used in part to calculate minimum warning and alert levels. To be statistically significant, the decrease in normal monitored bacteria count rate should be at either 1 sigma, 3 sigma, or 6 sigma below the background count rate, depending on how the user wants to operate the system.

EXAMPLE 4

Rancho Bernardo tap water was monitored for naturally occurring rod-shaped bacteria and produced an average count per minute of 120 and decreased to 10 counts per minute after about an hour after the water was adjusted to 0.1 Normal with the addition of NaOH. NaOH was used to simulate the toxic effects that potential toxic agent that terrorists may add to the water with a resultant die-off of the naturally occurring bacteria in the water. A simple 0.06% addition of commercial concentration of Laundry Chlorox may also be used to simulate a chemical attack as is described in EXAMPLE 5.

EXAMPLE 5

A system was spiked with bacteria at a concentration of 1,000 per milliliter to simulate normally occurring bacteria in the water and counts per minute of rod-shaped bacteria went from 1.05 to 28.8 after the spike of bacteria and remained at the higher level. Then the water was spiked to a dilution of 0.06% laundry Chlorox solution and the counts per minute of the rod-shaped bacteria decreased rapidly from 28.8 to 7.1, clearly showing the toxic effect.

While naturally occurring water borne bacteria may provide a good source of count rate to monitor for possible toxic agent attack, other naturally occurring microorganisms may be employed to perform the same function for the present invention, such as *algae, protozoa, or amoeba*.

While chemical toxins have been used to illustrate the present invention, it is clear that any toxic substance that materially changes the shape or scattering properties of the monitored microorganism, or that substantially change the nature of any related biofilm in the water system, may be used to practice the present invention, including but not limited to microbial toxins such as botulism, other chemical toxins not previously listed, and radiation generating toxins that can damage cell structure such as alpha, beta, or gamma generating compounds or elements.

While the invention has been described with respect to a limited number of embodiments, the specific features of one embodiment should not be attributed to other embodiments of the invention. No single embodiment is representative of all aspects of the inventions. Moreover, variations and modifications therefrom exist. The invention has been described in terms of water as a liquid, however any substantially clear liquid may be the media to monitor for toxins, such as process water used in manufacturing, sea water used for bathing, water that has added dissolved substances, such as sugars, alcohol, or other chemicals, or other liquids that may not have a water base, such as oils. Flowcells of different geometry can be used, light sources other then laser, such as LED, incandescent, mercury vapor, or multiple light sources, or multiple detectors can be used, and dedicated digital processors, other then common computers can be used to practice the present invention. In some embodiments, the devices are substantially free or essential free of any feature on specifically enumerated herein. Some embodiments of the method described herein consist of or consist essentially of the enumerated steps. The appended claims intend to cover all such variations and modifications as falling within the scope of the invention.

What is claimed:

1. A system for detecting an addition of a toxin to liquid, the system comprising:
    an optical axis;
    a target zone, the optical axis intersecting the target zone;
    at least one light source configured to generate a light beam and direct the light beam through the target zone;
    an optic lens system configured to collect light scattered by a particle associated with the toxin in the liquid in the target zone and direct the scattered light to at least one detector, the detector configured to detect the light and generate a digital signal; and
    a computer system coupled with the detector, the computer system configured to execute a set of programmed instructions to identify and classify the particle associated with the toxin, compare counts per unit time to a threshold, and generate an alarm, the instructions causing the computer system to:
    extract events from the digital signal;
    calculate the similarity between the extracted event and a known event;
    classify the event based on the similarity;
    calculate a new count rate for the classification type associated with the toxin;
    compare the new count rate to a threshold; and
    generate an alarm if the count rate falls below the threshold.

2. The system of claim 1, wherein the toxin is a chemical toxin.

3. The system of claim 1, wherein the toxin is a biotoxin.

4. The system of claim 1, wherein the toxin is a radiation generating toxin.

5. The system of claim 1, wherein similarity is determined by calculation of the coefficient of correlation between the extracted event and a known event.

6. The system of claim 1, wherein similarity is determined by calculation of pdist between the extracted event and a known event.

7. The system of claim 1, wherein similarity is determined by calculation of the ratios of outer pixels to inner pixels and comparing between the extracted event and a known event.

8. The system of claim 1, wherein the instructions are further configured to cause the computer system to extract events by causing the computer system to generate a intensity versus time vector (L-events vector) for the extracted event.

9. The system of claim 8, wherein the instructions are further configured to cause the computer system to extract events by causing the computer system to tuned differential vector from the L-events vector.

10. The system of claim 9, wherein the instructions are further configured to cause the computer system to extract events by causing the computer system to compare the tuned differential vector to a threshold.

11. The system of claim 10, wherein comparing the tuned differential vector to a threshold comprises comparing the tuned differential vector to a low threshold and then a high threshold.

12. The system of claim 10, wherein the instructions are further configured to cause the computer system to extract events by causing the computer system to begin counting subsequent frames received from the detector based on the comparison, and to determine an interval for the event based in the number of frames counted.

13. The system of claim 12, wherein the instructions are further configured to cause the computer system to extract events by causing the computer system to determine an event duration based in the number of frames counted and to compare the duration to a threshold.

14. The system of claim 13, wherein comparing the event duration to a threshold comprises comparing the event duration to a minimum and a maximum threshold.

15. The system of claim 13, wherein the instructions are further configured to cause the computer system to extract events by causing the computer system to locate a peak position frame for the event.

16. The system of claim 15, wherein the instructions are further configured to cause the computer system to extract events by causing the computer system to remove noise from the digital signal by summing on a pixel by pixel basis the peak position frame and the previous frame and subtracting (0.5 multiplied by the sum of corresponding pixels from the three frames before the peak event and 0.5 multiplied by the sum of corresponding pixels from the three frames after the event).

17. The system of claim 16, wherein the instructions are further configured to cause the computer system to extract events by causing the computer system to normalize the frame that results from the summing and subtracting.

18. The system of claim 17, wherein the instructions are further configured to cause the computer system to extract events by causing the computer system to correct the gain for the normalized frame.

19. The system of claim 18, wherein the instructions are further configured to cause the computer system to extract events by causing the computer system to correct dead pixels in the normalized frame.

20. The system of claim 1, wherein the instructions are further configured to cause the computer system to extract events by causing the computer system to perform a mean amplitude calculation on the normalized frame.

21. The system of claim 20, wherein the instructions are further configured to cause the computer system to extract events by causing the computer system to back rotate the normalized frame to the standard orientation of a major axis using a rotation angle.

22. The system of claim 1, wherein the instructions are further configured to cause the computer system to precondition the extracted events.

23. The system of claim 22, wherein the instructions are further configured to cause the computer system to precondition the extracted events by causing the computer system to generate a normalized array of events, each event of the array of events comprising a standard orientation, and to adjust the mean value of each event in the array of events.

24. The system of claim 23, wherein adjusting the mean value comprises adjusting the mean value to a predetermined value.

25. The system of claim 23, wherein the instructions are further configured to cause the computer system to precondition the extracted events by causing the computer system to perform log normal processing for each event of the array of events.

26. The system of claim 25, wherein the instructions are further configured to cause the computer system to precondition the extracted events by causing the computer system to readjust the mean for each event of the array of events after the log normal processing.

27. The system of claim 22, wherein the instructions are further configured to cause the computer system to precondition the extracted events by causing the computer system to generate a normalized array of events, each event of the array of events comprising a standard orientation, and to multiply each pixel time in the array of events by sin(scattering angle)^4.

28. The system of claim 27, wherein the instructions are further configured to cause the computer system to precondition the extracted events by causing the computer system to adjust the mean for each event in the array of events to a predetermined value.

29. The system of claim 1, wherein the instructions are further configured to cause the computer system to extract features for classification for the extracted event.

30. The system of claim 29, wherein the instructions are further configured to cause the computer system to extract features from the extracted events by causing the computer system to generate a normalized array of events, each event of the array of events comprising a standard orientation, and to use the entire frame corresponding to each event in the array of events for extraction.

31. The system of claim 29, wherein the instructions are further configured to cause the computer system to extract features from the extracted events by causing the computer system to generate a normalized array of events, each event of the array of events comprising a standard orientation, and to perform spatial transformation on each event in the array of events.

32. The system of claim 31, wherein the instructions are further configured to cause the computer system to extract features from the extracted events by causing the computer system to select either the RT-circular or RT-spoke data for classification.

33. The system of claim 1, wherein classifying the event comprises generating a Bio-Optical Signature.

34. A method of monitoring liquid for a toxin attack comprising:
- monitoring the liquid with a multi-angle light scattering device;
- classifying detected particles;
- generating a count rate for the classes of particles; and
- generating an alarm if the count rate falls below a threshold.

35. The method of claim 34, wherein classifying detected particles comprises:
- extracting events from the digital signal;
- calculating the similarity between the extracted event and a known event;
- classifying the event based on the similarity.

36. The method of claim 35, wherein similarity is determined by calculation of the coefficient of correlation between the extracted event and a known event.

37. The method of claim 35, wherein similarity is determined by calculation of pdist between the extracted event and a known event.

38. The method of claim 35, wherein similarity is determined by calculation of the ratios of outer pixels to inner pixels and comparing between the extracted event and a known event.

39. The method of claim 35, wherein extracting events comprises generating an intensity versus time vector (L-events vector) for the extracted event.

40. The method of claim 39, wherein extracting events comprises generating a tuned differential vector from the L-events vector.

41. The method of claim 40, wherein extracting events comprises comparing the tuned differential vector to a threshold.

42. The method of claim 41, wherein comparing the tuned differential vector to a threshold comprises comparing the tuned differential vector to a low threshold and then a high threshold.

43. The method of claim 41, wherein extracting events comprises counting subsequent frames received from a detector based on the comparison, and to determining an interval for the event based in the number of frames counted.

44. The method of claim 43, extracting events comprises determining an event duration based in the number of frames counted and to compare the duration to a threshold.

45. The method of claim 44, wherein comparing the event duration to a threshold comprises comparing the event duration to a minimum and a maximum threshold.

46. The method of claim 44, wherein extracting events comprises locating a peak position frame for the event.

47. The method of claim 46, wherein extracting events comprises removing noise from the digital signal by summing on a pixel by pixel basis the peak position frame and the previous frame and subtracting (0.5 multiplied by the sum of corresponding pixels from the three frames before the peak event and 0.5 multiplied by the sum of corresponding pixels from the three frames after the event).

48. The method of claim 47, wherein extracting events comprises normalizing the frame that results from the summing and subtracting.

49. The method of claim 48, wherein extracting events comprises correcting the gain for the normalized frame.

50. The method of claim 49, wherein extracting events comprises correcting dead pixels in the normalized frame.

51. The method of claim 35, wherein extracting events comprises performing a mean amplitude calculation on the normalized frame.

52. The method of claim 51, wherein extracting events comprises back rotating the normalized frame to the standard orientation of a major axis using a rotation angle.

53. The method of claim 35, further comprising preconditioning the extracted events.

54. The method of claim 53, wherein preconditioning the extracted events comprises generating a normalized array of events, each event of the array of events comprising a standard orientation, and adjusting the mean value of each event in the array of events.

55. The method of claim 54, wherein adjusting the mean value comprises adjusting the mean value to a predetermined value.

56. The method of claim 54, wherein preconditioning the extracted events comprises performing log normal processing for each event of the array of events.

57. The method of claim 56, wherein preconditioning the extracted events comprises readjusting the mean for each event of the array of events after the log normal processing.

58. The method of claim 53, wherein preconditioning the extracted events comprises generating a normalized array of events, each event of the array of events comprising a standard orientation, and multiplying each pixel time in the array of events by $\sin(\text{scattering angle})^4$.

59. The method of claim 58, wherein preconditioning the extracted events comprises adjusting the mean for each event in the array of events to a predetermined value.

60. The method of claim 35, further comprising extracting features for classification for the extracted event.

61. The method of claim 60, wherein extracting features from the extracted events comprises generating a normalized array of events, each event of the array of events comprising a standard orientation, and using the entire frame corresponding to each event in the array of events for extraction.

62. The method of claim 60, wherein extracting features from the extracted events comprises generating a normalized array of events, each event of the array of events comprising a standard orientation, and performing spatial transformation on each event in the array of events.

63. The method of claim 62, wherein extracting features from the extracted events comprises selecting either the RT-circular or RT-spoke data for classification.

64. The method of claim 35, wherein classifying the event comprises generating a Bio-Optical Signature.

* * * * *